(12) United States Patent
Robbins et al.

(10) Patent No.: US 12,700,485 B2
(45) Date of Patent: Aug. 4, 2026

(54) SYSTEMS AND METHODS FOR AUGMENTED REALITY (AR) ARTIFICIAL INTELLIGENCE (AI)-CONSTRUCTED, INTERACTIVE THREE-DIMENSIONAL (3D) HUMAN BODY MODELING

(71) Applicant: The Travelers Indemnity Company, Hartford, CT (US)

(72) Inventors: Michael H. Robbins, Westhampton, NY (US); Ryan M. Scanlon, East Hampton, CT (US); Matthew C. Paulette, Bristol, CT (US); Douglas L. Roy, Plantsville, CT (US); Amanda L. Wadleigh, Rockaway, NJ (US); Peter Dahl, Florham Park, NJ (US)

(73) Assignee: The Travelers Indemnity Company, Hartford, CT (US)

( * ) Notice: Subject to any disclaimer, the term of this patent is extended or adjusted under 35 U.S.C. 154(b) by 35 days.

(21) Appl. No.: 18/768,327

(22) Filed: Jul. 10, 2024

(65) Prior Publication Data

US 2026/0018265 A1 Jan. 15, 2026

(51) Int. Cl.

| | |
|---|---|
| *G16H 10/60* | (2018.01) |
| *A61B 5/00* | (2006.01) |
| *G06F 40/279* | (2020.01) |
| *G06F 40/40* | (2020.01) |
| *G06Q 40/08* | (2012.01) |
| *G06T 17/20* | (2006.01) |
| *G06T 19/00* | (2011.01) |
| *G06T 19/20* | (2011.01) |
| *G06V 30/19* | (2022.01) |
| *G16H 50/50* | (2018.01) |

(52) U.S. Cl.
CPC ............. *G16H 10/60* (2018.01); *A61B 5/743* (2013.01); *G06F 40/279* (2020.01); *G06F 40/40* (2020.01); *G06Q 40/08* (2013.01); *G06T 17/20* (2013.01); *G06T 19/006* (2013.01); *G06T 19/20* (2013.01); *G06V 30/19173* (2022.01); *G16H 50/50* (2018.01); *G06T 2200/24* (2013.01); *G06T 2210/41* (2013.01); *G06T 2219/2016* (2013.01)

(58) Field of Classification Search
None
See application file for complete search history.

(56) References Cited

U.S. PATENT DOCUMENTS

| | | | | |
|---|---|---|---|---|
| 11,721,035 B2* | 8/2023 | Do | ......................... | G06F 1/1626 |
| | | | | 345/633 |
| 2020/0293174 A1* | 9/2020 | Diaz | ...................... | A61B 34/25 |
| 2023/0368878 A1* | 11/2023 | Molenda | ................ | G16H 70/60 |

FOREIGN PATENT DOCUMENTS

| | | | | |
|---|---|---|---|---|
| CN | 108846892 A | * 11/2018 | ............. | G06T 17/00 |

* cited by examiner

*Primary Examiner* — Mamon Obeid
*Assistant Examiner* — Ashley Elizabeth Evans
(74) *Attorney, Agent, or Firm* — Rowan Tree Law Group, PLLC; Carson C.K. Fincham

(57) ABSTRACT

An Augmented Reality (AR) and Artificial Intelligence (AI)-constructed, interactive three-dimensional (3D) human body modeling system that analyzes data descriptive of medical records and generates an interactive 3D human body model output via AR. The 3D human body model may have body part-specific interactive medical record data embedded therein, permitting a user to quickly, easily, and intuitively navigate the model to identify relevant medical status for the modelled individual.

19 Claims, 19 Drawing Sheets

300

*300*

Chart Summary:
21-year old male involved in accident on October 1, 2019. Evaluated for head and spine injuries. Right knee pain on December 2, 2020, and June 2, 2021. Surgery on December 13, 2021: anthroscopy, meniscectomy, chondroplasty, synovectomy, plica evaluation. Improved pain but experienced random flare-ups. Poor prognosis, therapy knee treatment required.

300

320e

370

Chart Summary:
21-year old male involved in accident on October 1, 2019. Evaluated for head and spine injuries. Right knee pain on December 2, 2020, and June 2, 2021. Surgery on December 13, 2021: anthroscopy, meniscectomy, chondroplasty, synovectomy, plica evaluation. Improved pain but experienced random flare-ups. Poor prognosis, therapy knee treatment required.

320-6

324a

Treatment Type: Injection
Date:11/12/2019
Location: Upper Arm Tdap

Diphtheria, tetanus, and pertussis (DTaP) vaccine administered. No reported injection site reaction.

344-1a

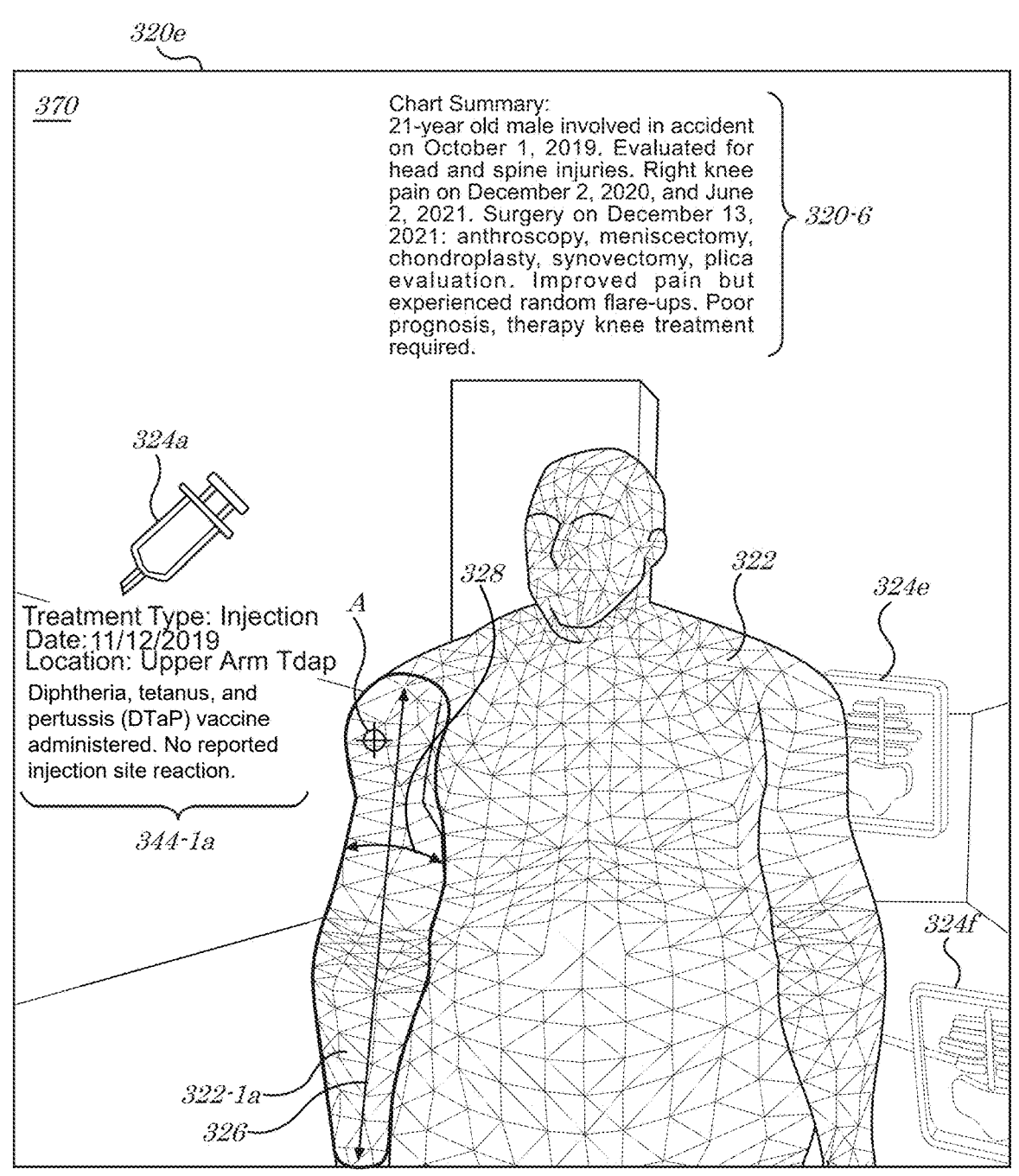

Height: 4'6"

Weight: 80lbs

Menu

*300*

*320k*

*370*

*324e*

*322*

*320-10*

*320-1*

AVirTRAVian Man EA&ET

Resume    Quit

*B*

9:26

*400*

IDENTIFY MEDICAL RECORDS — *402*

COMPUTE MEDICAL RECORD DATA ELEMENTS — *404*

CREATE/POPULATE DATA STRUCTURE — *406*

*408*
MORE DATA ELEMENTS

YES

NO

RECEIVE REQUEST — *410*

GENERATE 3D HUMAN BODY MODEL — *412*

OUTPUT 3D HUMAN BODY MODEL — *414*

OUTPUT BODY PART-SPECIFIC MEDICAL EVENT INDICATOR — *416*

RECEIVE SELECTION OF FIRST BODY PART — *418*

OUTPUT REPRESENTATION OF FIRST MEDICAL RECORD DATA — *420*

*640b*

*640c*

AR/AI 3D HUMAN BODY MODEL MODULE

*640d*

*640e*

SYSTEMS AND METHODS FOR AUGMENTED REALITY (AR) ARTIFICIAL INTELLIGENCE (AI)-CONSTRUCTED, INTERACTIVE THREE-DIMENSIONAL (3D) HUMAN BODY MODELING

BACKGROUND

The review of medical records is a time-consuming, complicated task that can be prone to errors due to the volume of detailed information in the records. Whether the review is conducted for diagnosis, treatment, insurance claim handling, and/or other purposes, the delay created by the task can cause significant losses in revenue and/or profits or can cause or exacerbate medical symptoms or issues. The review or summarization of medical records is made more difficult due to the format and nature of the data that is recorded. For liability, statutory and/or regulatory, and/or other reasons not directly related to the underlying medical data, for example, medical records are often convoluted, complex, and overly detailed. Some previous efforts have attempted to reduce the clutter or "noise" associated with medical record review by utilizing Current Procedural Terminology (CPT) codes or other medical event codes to better group or identify medical records data. While these efforts have contributed to reducing the typical problems with medical record review and analysis, enhanced review procedures remain a significant time and expense load for various entities in the medical and insurance industries.

BRIEF DESCRIPTION OF THE DRAWINGS

The figures depict embodiments for purposes of illustration only. One skilled in the art will readily recognize from the following description that alternative embodiments of the systems and methods illustrated herein may be employed without departing from the principles described herein, wherein:

FIG. 3A, FIG. 3B, FIG. 3C, FIG. 3D, FIG. 3E, FIG. 3F, FIG. 3G, FIG. 3H, FIG. 3I, FIG. 3J, and FIG. 3K are diagrams of an example Augmented Realty (AR) output system according to some embodiments;

DETAILED DESCRIPTION

I. Introduction

Figure 1:
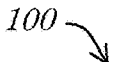
FIG. 1 is a block diagram of a system according to some embodiments.
Figure 1:
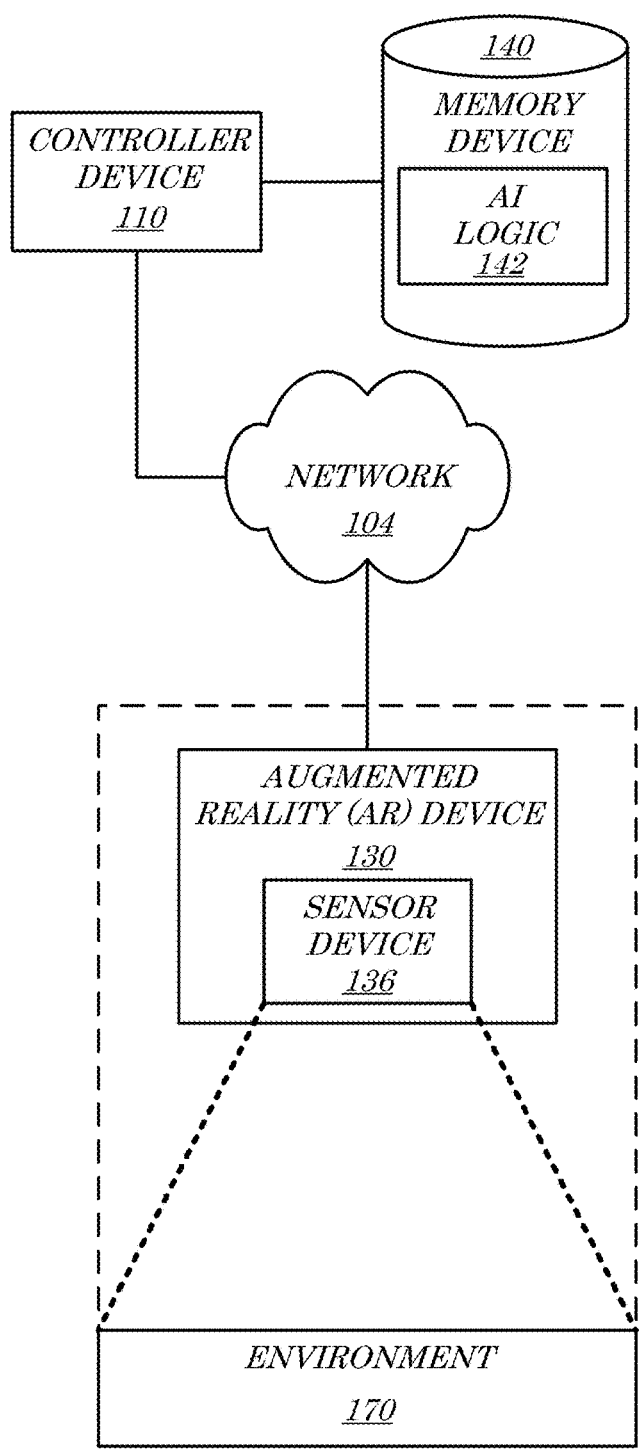

Previous efforts to streamline medical record review and summarization have focused on utilizing data codes to group or summarize data elements at a high level. These efforts are necessarily dependent upon the underlying codes being populated correctly, however, and are limited to pre-existing mappings being hard-coded for each specific code. The summarization efforts, while capable of reducing the volume of materials that must be examined by human personnel, still require the human personnel to both read through and comprehend the coded mappings/summaries. Medical record review and analysis is accordingly still prone to human errors and still consumes a great deal of time to process.

In accordance with embodiments herein, these and other deficiencies of existing systems are remedied by providing systems, apparatus, methods, and articles of manufacture for Augmented Reality (AR) and Artificial Intelligence (AI)-constructed, interactive three-dimensional (3D) human body modeling. In some embodiments, for example, an AR/AI-based 3D human body modeling system may utilize various sensors and wearable (e.g., head-mounted) computer hardware to: (i) identify medical record data (e.g., for a particular individual/patient), (ii) identify (e.g., compute) a plurality of medical record data elements descriptive of discrete medical record events for the individual (e.g., by executing a medical record LLM), (iii) create and/or populate a 3D human body model medical record data structure (e.g., that maps each discrete medical record event to a specific portion of a body of the individual), (iv) receive a request to generate a 3D human body model representing the individual, (v) generate and/or output the 3D human body model representing the individual (e.g., via an AR headset and/or utilizing the populated 3D human body model medical record data structure), (vi) output a representation of a first one of the discrete medical record events for the individual at an AR location corresponding to a first body part of the individual, (vii) receive an indication of a selection of the first body part of the individual, and/or (viii) output (e.g., via the AR headset) a representation of a first one of the plurality of medical record data elements corresponding to the first one of the discrete medical record events for the individual.

In accordance with some embodiments, the application of AR/AI-based 3D human body modeling system processing, as described herein, may provide a reduction in computer processing resources, a reduction in necessary memory storage requirements, and other technical improvements with respect to existing systems that store large quantities of medical record data. The particular AR/AI-based 3D human body modeling systems and methods described herein may, for example, permit available wearable AR device processing and memory resources to be utilized to permit 3D visualization of medical record data without requiring access to mass storage devices, large capital outlays, and/or specialized training. According to some embodiments, an untrained or minimally-trained end user may be presented with a user-friendly 3D human body model that visually summarizes and represents medical data of a modeled individual. In such a manner, for example, specialized personnel may no longer be necessary to conduct every medical records analysis, greatly reducing costs, reducing the amount of time required to conduct medical record investigation analysis and/or assessments, and/or reducing bandwidth constraints in electronic networks.

II. AR and AI-Constructed 3D Human Body Modeling Systems

Referring first to FIG. 1, a block diagram of a system 100 according to some embodiments is shown. In some embodiments, the system 100 may comprise a network 104 via which a controller device 110 communicates with an Augmented Reality (AR) device 130. In some embodiments, the AR device 130 may comprise one or more sensor devices 136, such as an imaging and/or other input device. According to some embodiments, the sensor device 136 and/or the AR device 130 may be in communication with (e.g., via the network 104) and/or may provide indications of data acquired by the sensor device 136 to the controller device 110. In some embodiments, the controller device 110 and/or the AR device 130 may be in communication with (e.g., via the network 104) a memory device 140 (e.g., storing AI logic 142). In accordance with various embodiments herein, the AR device 130 and/or the sensor device 136 may be utilized to direct, manage, and/or define the capture of imagery (and/or other sensor data) of an environment 170 and/or one or more objects (not separately shown) thereof. In some embodiments, the imagery/data captured by the sensor device 136 may be provided from the AR device 130 to the controller device 110 for imagery/sensor data analysis and execution of stored analysis rules and/or logic (e.g., the AI logic 142). In such a manner, for example, data descriptive of the objects (e.g., surfaces, features, attributes, etc.) may be input into the system 100 and utilized to identify/classify the objects and/or to evaluate (e.g., map) the environment 170. In some embodiments, the AI logic 142 and/or the memory device 140 may reside in and/or form part of the AR device 130. According to some embodiments, the AR device 130 may be utilized to tag and/or otherwise assign or associate sensor data with one or more objects, portions, and/or locations (e.g., points, lines, and/or areas) of the environment 170. In such a manner, for example, various forms and/or tiers or layers of data may be automatically embedded and/or linked to locations within the environment 170. According to some embodiments, the AI logic 142 may be utilized to identify, classify, and/or summarize medical record data (not separately show; e.g., stored in the memory device 140) and provide physically-related medical data metrics to the AR device 130, such that the AR device 130 may generate a 3D human body model (not shown) within the environment 170.

Fewer or more components 104, 110, 130, 136, 140, 142, 170 and/or various configurations of the depicted components 104, 110, 130, 136, 140, 142, 170 may be included in the system 100 without deviating from the scope of embodiments described herein. In some embodiments, the components 104, 110, 130, 136, 140, 142, 170 may be similar in configuration and/or functionality to similarly named and/or numbered components as described herein. In some embodiments, the system 100 (and/or portions thereof) may comprise an AR/AI-based 3D human body modeling program, system, and/or platform programmed and/or otherwise configured to execute, conduct, and/or facilitate the methods 400, 700 of FIG. 4 and/or FIG. 7 herein, and/or portions or combinations thereof.

The network 104 may, according to some embodiments, comprise a Local Area Network (LAN; wireless and/or wired), cellular telephone, Bluetooth® and/or Bluetooth® Low Energy (BLE), Near Field Communication (NFC), and/or Radio Frequency (RF) network with communication links between the controller device 110, the AR device 130, the sensor device 136, and/or the memory device 140. In some embodiments, the network 104 may comprise direct communication links between any or all of the components 110, 130, 136, 140 of the system 100. The sensor device 136 may, for example, be directly interfaced or connected to the AR device 130 via one or more wires, cables, wireless links, and/or other network components, such network components (e.g., communication links) comprising portions of the network 104. In some embodiments, the network 104 may comprise one or many other links or network components other than those depicted in FIG. 1. The sensor device 136 and/or the AR device 130 may, for example, be connected to the controller device 110 via various cell towers, routers, repeaters, ports, switches, and/or other network components that comprise the Internet and/or a cellular telephone (and/or Public Switched Telephone Network (PSTN)) network, and which comprise portions of the network 104.

While the network 104 is depicted in FIG. 1 as a single object, the network 104 may comprise any number, type, and/or configuration of networks that is or becomes known or practicable. According to some embodiments, the network 104 may comprise a conglomeration of different sub-networks and/or network components interconnected, directly or indirectly, by the components 110, 130, 136, 140 of the system 100. The network 104 may comprise one or more cellular telephone networks with communication links between the sensor device 136 and the controller device 110, for example, and/or may comprise a BLE, NFC, RF, and/or "personal" network comprising short-range wireless communications between the sensor device 136 and the AR device 130, for example.

In some embodiments, the controller device 110 may comprise an electronic and/or computerized controller device, such as a computer server and/or server cluster communicatively coupled to interface with the AR device 130 and/or the sensor device 136 (directly and/or indirectly). The controller device 110 may, for example, comprise one or more PowerEdge™ M910 blade servers manufactured by Dell®, Inc. of Round Rock, TX, which may include one or more Eight-Core Intel® Xeon® 7500 Series electronic processing devices. According to some embodiments, the controller device 110 may be located remotely from the AR device 130 and/or the environment 170. The controller device 110 may also or alternatively comprise a plurality of electronic processing devices located at one or more various sites and/or locations (e.g., a distributed computing and/or processing network), such as the environment 170.

According to some embodiments, the controller device 110 (and/or the AR device 130) may store and/or execute specially-programmed instructions to operate in accordance with embodiments described herein. The controller device 110 may, for example, execute one or more programs (such as the AI logic 142) that identifies, summarizes, categories, and/or otherwise processes medical record data and/or builds and/or populates a data structure (not separately shown; e.g., within the memory device 140). In some embodiments, the AR device 130 (and/or the controller device 110) may also or alternatively execute one or more programs that facilitate and/or cause the automatic detection, verification, data capture, and/or data analysis of the environment 170, and/or the generation, projection, and/or outputting of a 3D human body model in the environment 170 (e.g., via AR), as described herein. According to some embodiments, the controller device 110 may comprise a computerized processing device, such as a PC, laptop computer, computer server, and/or other network or electronic device, operated to manage and/or facilitate medical record data identification, acquisition, sorting, filtering, analysis, decoding, categorizing, and/or organization in accordance with embodiments described herein.

In some embodiments, the AR device 130 may comprise any type or configuration of device, sensor, and/or system that is capable of capturing imagery and/or other data descriptive of the environment 170 and/or the objects, portions, and/or attributes thereof, and/or that is operable to project, generate, and/or output AR imagery and/or interfaces (not shown) in and/or with respect to the environment 170. The AR device 130 may, in some embodiments, comprise a wearable computing device that provides AR (and/or Mixed Reality (MR) capabilities to a wearer thereof. The AR device 130 may, for example, comprise a Meta® Quest 3™ available from Meta Platforms, Inc., doing business as Meta, and formerly named Facebook, Inc., of Menlo Park, CA or a Magic Leap 2™ wearable AR unit available from Magic Leap, Inc. of Plantation, FL. The Magic Leap 2™ comprises (none of the following being shown in FIG. 1) an electronic processing device, a built-in memory device (e.g., two hundred and fifty-six Gigabyte (256 GB)), a twelve point six Megapixel (12.6 MP) autofocus Red-Green-Blue (RGB) video camera (e.g., with a seventy degree (70°) field of View (FoV)), built-in audio speakers, four (4) IMU sensors (e.g., three-axis (3-axis) accelerometer and gyroscope; two (2) three-axis (3-axis) magnetometers; and two (2) altimeters), a see-through display (e.g., head-mounted, with one thousand four hundred forty by one thousand seven hundred sixty pixel (1440×1760) resolution and twenty to two thousand nits (20-2000) brightness, and a battery providing power to the various components. In some embodiments, the AR device 130 may comprise a wireless communication device (e.g., for communications via the network 104) and/or a paired hand-held controller/pointer device (e.g., six (6)-degrees of freedom). According to some embodiments, the AR device 130 may comprise a handheld and/or mobile (e.g., and/or non-wearable) computing device capable of providing AR, Mixed Reality (MR), and/or Virtual Reality (VR) output (and/or accepting input via AR, MR, and/or VR interfaces) such as an iPad® manufactured by Apple®, Inc. of Cupertino, CA, and/or cellular and/or wireless telephones or "smart" phones, such as an iPhone® (also manufactured by Apple®, Inc.) or an Optimus™ S smart phone manufactured by LG® Electronics, Inc. of San Diego, CA, and running the Android® operating system from Google®, Inc. of Mountain View, CA. In some embodiments, the sensor device 136 may comprise and/or include any or all of the input devices of the AR device 130.

The sensor device 136, in some embodiments, may comprise any type or configuration of device, sensor, and/or object that is capable of capturing imagery and/or other data descriptive of the environment 170 and/or the objects, portions, and/or attributes thereof. The sensor device 136 may comprise, for example, a camera (e.g., coupled to and/or integral with the AR device 130), such as the Pro 12MP or Dual 12MP camera available on the iPhone® 12 Pro or iPhone® 12, respectively, manufactured by Apple®, Inc. of Cupertino, CA) and/or a ranging device, such as a Light Detection and Ranging (LiDAR) device. In some embodiments, the sensor device 136 may comprise a stand-alone device (e.g., separate from the AR device 130). In some embodiments, the sensor device 136 may comprise a multispectral imaging device capable of capturing three- or four-band imagery data (e.g., RGB plus Near IR). The imagery and/or other data captured by the sensor device 136 may generally comprise any type, quantity, and/or format of photographic, video, and/or other sensor data descriptive of the environment 170 and/or the objects, portions, and/or attributes thereof. According to some embodiments, the data captured and/or acquired by the sensor device 136 may comprise one or more images (still, and/or video frames) captured from different positions and/or locations in or proximate to and/or in the environment 170, such as a plurality of individual images taken at different bearings and/or elevations from a given position.

In some embodiments, the sensor device 136 may also or alternatively comprise a server and/or datastore (e.g., the controller device 110 and/or the memory device 140) that is configured to provide the imagery and/or other data descriptive of the environment 170. The sensor device 136 may comprise, for example, a third-party and/or vendor device configured to supply imagery and/or other sensor data acquired from various cameras, sensors, and/or other sources. According to some embodiments, the sensor device 136 may comprise the AR device 130 incorporating sensor and AR capabilities, such as any type or configuration of computing, mobile electronic, network, user, and/or communication device that is or becomes known or practicable. The sensor device 136 may, in some embodiments, comprise one or more tablet computers, such as the iPad® manufactured by Apple®, Inc. of Cupertino, CA, and/or cellular and/or wireless telephones or "smart" phones, such as the iPhone® (also manufactured by Apple®, Inc.) or the Optimus™ S smart phone manufactured by LG® Electronics, Inc. of San Diego, CA, and running the Android® operating system from Google®, Inc. of Mountain View, CA.

In some embodiments, the sensor device 136 may comprise one or more devices owned and/or operated by one or more users, such as a remote worker (e.g., a medical records investigator), employee, etc. According to some embodiments, the sensor device 136 may communicate with the controller device 110 via the network 104 to provide imagery and/or other data captured by the sensor device 136 for analysis and/or assessment of the environment 170. According to some embodiments, the sensor device 136 may store and/or execute specially programmed instructions (such as a mobile device application) to operate in accordance with embodiments described herein. The sensor device 136 may, for example, execute one or more mobile device programs that activate and/or control the sensor device 136 and/or that analyze imagery and/or other data of the environment 170, e.g., to identify, locate, and/or classify one or more of the objects, portions, and/or attributes of the environment 170, and/or to position various AR elements and/or interface components within the environment 170 via AR projection and/or output. In some embodiments, the sensor device 136 may provide data descriptive of the environment 170 to the AR device 130 so that the AR device 130 may properly embed, overlap, and/or map virtual interface and/or output elements into the environment 170.

In some embodiments, the controller device 110 and/or the AR device 130 (and/or the sensor device 136) may be in communication with the memory device 140. The memory device 140 may store, for example, medical record data, location data (such as coordinates, distances, etc.), security access protocol and/or verification data, object classification data, medical record analysis and/or assessment data and/or logic (such as medical record mapping and/or analysis rules; e.g., the AI logic 142), and/or instructions that cause various devices (e.g., the controller device 110, the AR device 130, and/or the sensor device 136) to operate in accordance with embodiments described herein. In some embodiments, the memory device 140 may comprise any type, configuration, and/or quantity of data storage devices that are or become known or practicable. The memory device 140 may, for example, comprise an array of optical and/or solid-state hard drives configured to store medical record data, 3D human body model data storage structure instructions, templates, and/or objects, and/or data descriptive of the environment 170, device identifier data, user identifier data, the AI logic 142 and/or training data therefor, image (and/or other sensor data) analysis data, image (and/or other sensor data) processing data, and/or various operating instructions, drivers, etc. In some embodiments, the memory device 140 may comprise a standalone and/or networked data storage device, such as a solid-state and/or non-volatile memory card (e.g., a Secure Digital (SD) card, such as an SD Standard-Capacity (SDSC), an SD High-Capacity (SDHC), and/or an SD extended-Capacity (SDXC), and any various practicable form factors, such as original, mini, and micro sizes, such as those available from Western Digital Corporation of San Jose, CA). While the memory device 140 is depicted as a standalone component of the system 100 in FIG. 1, the memory device 140 may comprise multiple components. In some embodiments, a multi-component memory device 140 may be distributed across various devices and/or may comprise remotely dispersed components. Any or all of the AR device 130, the sensor device 136, and/or the controller device 110 may comprise the memory device 140 or a portion thereof, for example.

According to some embodiments, the environment 170 may comprise any location desired for viewing and/or interacting with a 3D human body model (and/or other multi-dimensional human body models, such as two-dimensional (2D)), e.g., generated and/or output by the AR device 130. In some embodiments, the environment 170 may be identified by one or more location parameters, such as an address, postal code, map quadrant, a particular building and/or structure, a room, and/or one or more coordinates and/or other identifiers (e.g., a unique georeferenced location identifier, such as latitude and longitude coordinates and/or a Global Positioning System (GPS) coordinate). According to some embodiments, the environment 170 may comprise the one or more objects, portions, locations, areas, and/or attributes. In the case that the environment 170 comprises a room (or other interior structural space), for example, the objects may comprise various furnishings (e.g., moveable objects, such as couches (e.g., sofas), chairs, tables, lamps, rugs, etc.), materials, such as flooring or wall coverings (e.g., structural finishing), fixtures (e.g., plumbing, electrical, and/or other fixtures), work devices (such as computers, peripherals, input devices, output devices, tools, and/or machinery), and/or features, such as windows, doors, doorways, niches, coffers, stairways, fireplaces, etc. According to some embodiments, the environment 170 may be identified by a unique identifier and/or code that is stored (e.g., in the memory device 140) in relation to (e.g., creating a stored link with) the environment 170 and/or its associated location parameters.

Figure 2:
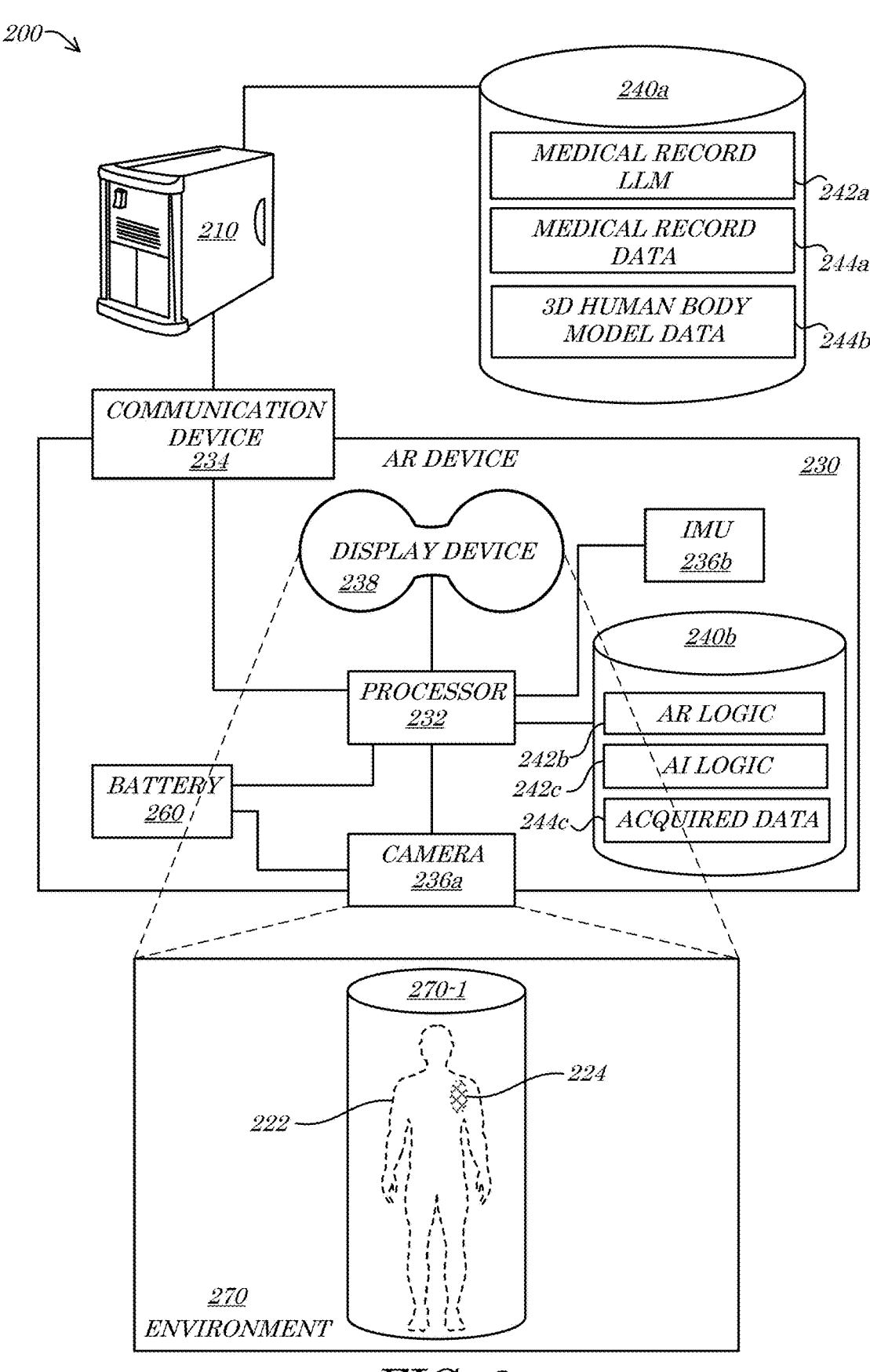
FIG. 2 is a block diagram of a system according to some embodiments.

Turning to FIG. 2, a diagram of a system 200 according to some embodiments is shown. In some embodiments, the system 200 may comprise an AR/AI-based 3D human body modeling system similar to the system of FIG. 1 herein. The system 200 may comprise, for example, a server 210 programmed and/or operable to facilitate and/or cause the generation of a 3D human body model 222 (e.g., comprising at least one body part indicator 224), e.g., by cooperatively operating and/or via communication with (e.g., via one or more wired and/or wireless networks) an AR device 230. In some embodiments, the AR device 230 may comprise a processor 232 (e.g., an electronic processing device such as a CPU), a communication device 234, and/or one or more sensors and/or input devices, such as a camera 236a and/or an Inertial Measurement Unit (IMU) 236b. According to some embodiments, the AR device 230 may comprise a display device 238 that generates, projects, and/or otherwise outputs the 3D human body model 222 (and/or the body part indicator 224 thereof). In some embodiments, the server 210 may be in communication with and/or comprise a first memory device 240a and/or the AR device 230 may comprise and/or be in communication with a second memory device 240b. The memory devices 240a-b may store, for example, various programs 242a-c and/or data 244a-c. As depicted for purposes of non-limiting example, the first memory device 240a may store a first program or medical record LLM 242a, first or medical record data 244a, and/or second or 3D human body model data 244b. In some embodiments, the second memory device 240b may store a second program or AR logic 242b, a third program or AI logic 242c, and/or third or acquired data 244c. According to some embodiments, the AR device 230 may comprise a battery 260 (and/or other power source) that generates and/or provides power to one or more of the onboard components 232, 234, 236a-b, 238, 240b of the AR device 230.

In some embodiments, the server 210 may execute the medical record LLM 242a to produce, identify, and/or define the 3D human body model data 244b (and/or underlying data structure thereof). The medical record LLM 242a may be trained and/or specially-programmed, for example, to utilize the medical record data 244a as input to provide AI-powered summarization, categorization, and/or analysis of the medical record data 244a. According to some embodiments, the medical record data 244a may comprise data descriptive of a plurality of discrete medical record events for one or more individuals. In some embodiments, the medical record LLM 242a may process the medical record data 244a to identify and/or define a plurality of medical record data elements descriptive of the plurality of discrete medical record events. According to some embodiments, the medical record LLM 242a may build, construct, and/or populate a data structure to store the plurality of medical record data elements, thereby defining the 3D human body model data 244b. In some embodiments, the 3D human body model data 244b may comprise data and/or data storage elements that map each discrete medical record event to a specific portion of a body of the individual and/or that define dimensional data (measured and/or derived) for the specific portion of a body of the individual.

According to some embodiments, the AR device 230 may comprise a mobile and/or wearable electronic device, such as smart glasses, equipped with one or more built-in and/or coupled devices, such as the built-in camera 236a and/or the display device 238 (e.g., a see-through or AR-enabled display device). In some embodiments, the camera 236a may be utilized (e.g., as directed and/or controlled by the AR device 230) to acquire image data (and/or other sensor data, such as distance measurements) from an environment 270. In some embodiments the captured data may comprise a plurality of related and/or overlapping images, a stitched image, and/or other data elements, such as coordinate, distance, location, temperature, color, and/or other data arrays, matrices, lists, etc. The camera 236a (and/or other type of sensor; e.g., a ToF sensor) may be coupled and/or disposed, for example, to capture data descriptive of the environment 270, e.g., comprising and/or defining one or more particular locations 270-1.

According to some embodiments, the AR device 230 may comprise a wearable mobile electronic device disposed at or proximate to the environment 270 and/or may be operated by a first user or "wearer" (not shown), such as a medical professional or a claims adjuster conducting an investigation regarding the medical status/history of the individual (e.g., at least one individual described by the medical record data 244a). In some embodiments, data acquired by the camera 236a and/or the IMU 236b may be stored in the second memory device 240b (e.g., as the acquired data 244c and/or a portion thereof) and/or processed in accordance with the AR logic 242b and/or the AI logic 242c. According to some embodiments, data stored and/or populated in the 3D human body model data 244*b* may be accessed and/or received by the AR device 230 and such data may also or alternatively be processed in accordance with the AR logic 242*b* and/or the AI logic 242*c*. The AR device 230 may, in some embodiments, execute and/or apply the AI logic 242*c* to identify, apply, resolve, and/or process one or more rules and/or rule sets coded to categorize and/or identify data descriptive of the environment 270 (and/or one or more specific locations 270-1 thereof). The AR device 230 (and/or the processor 232 thereof) may execute the AI logic 242*c*, for example, by applying a trained AI model to the acquired data 244*c* to generate and/or define a 3D model of the environment 270 (e.g., a 3D point cloud, Digital Elevation Model (DEM), 3D mesh model, etc.). According to some embodiments, the AR device 230 (and/or the processor 232 thereof) may execute the AI logic 242*c* by utilizing the 3D human body model data 244*b* to define and/or output the 3D human body model 222.

According to some embodiments, the AR logic 242*b* may be executed (e.g., by the AR device 230 and/or the processor 232 thereof) to dynamically integrate output descriptive of the processing results of the AI logic 242*c* via the display device 238. In the case that the display device 238 comprises a see-through and/or AR-enabled display, for example, the 3D human body model 222 may be output via the display device 238 in a manner so that it appears (e.g., to the wearer) to be superimposed or positioned in a Field of View (FoV) of the display device 238 (represented by dotted lines in FIG. 2) in the real-world environment 270 (e.g., AR or AR projection). The 3D human body model 222 may be projected and/or output to appear to be positioned at the particular location 270-1 which may, for example, comprise a point, line, area, and/or volume (the particular location 270-1 is depicted in FIG. 2 as a volume to represent the volumetric space that the 3D human body model 222 may occupy, solely for purposes of example) disposed at a certain distance from the wearer (e.g., a default distance of five feet (5-ft.) from the wearer. In some embodiments, the display device 238 may comprise one or more eye-tracking cameras (not separately shown; e.g., the camera 236*a* and/or one or more additional or alternative cameras not shown) that provide data to the processor 232 so that the AR logic 242*b* may actively move or reorient output to match the location in the environment 270 based on the eye movements/gaze of the wearer of the AR device 230.

In some embodiments, the IMU 236*b* may track and/or monitor movements of the AR device 230 such that the current position and FoV with respect to the environment 270 may be accurately determined and updated. In such a manner, for example, new data captured by the camera 236*a* may be utilized to append to an existing model (or partial model), such as a point cloud descriptive of the environment 270, and/or the 3D human body model 222 may be appropriately output (re-output/moved) via the display device 238 to correspond with portions or locations of the environment 270 (e.g., the particular location 270-1) that are being viewed by the wearer.

According to some embodiments, the AR device 230 (and/or the processor 232 thereof) may execute the AI logic 242*c* (e.g., utilizing the 3D human body model data 244*b*) to define the 3D human body model 222 (e.g., one or more modeled body dimensions thereof) and may execute the AR logic 242*b* to place and/or position the 3D human body model 222 within the environment 270 (e.g., at the particular location 270-1) via the display device 238 (e.g., AR projection/output). In some embodiments, the 3D human body model 222 may comprise an interactive display and/or interface that not only outputs information, such as data (e.g., images, graphics, audio/video, text, etc.) represented by and/or comprising the body part indicator 224, but that also permits the wearer/user to interact with such elements, e.g., to provide and/or define requests, menu selections, etc. In such a manner, for example, the AI analysis of the medical record data 244*a* by the server 210 may be utilized by the AR device 230 to generate, define, and/or output the 3D human body model 222 that permits the user/wearer to easily visualize and analyze the medical history and/or status of the modeled individual.

Fewer or more components 210, 230, 232, 234, 236*a-b*, 238, 240*a-b*, 242*a-c*, 244*a-c*, 260, 270, 270-1 and/or various configurations of the depicted components 210, 230, 232, 234, 236*a-b*, 238, 240*a-b*, 242*a-c*, 244*a-c*, 260, 270, 270-1 may be included in the system 200 without deviating from the scope of embodiments described herein. In some embodiments, the components 210, 230, 232, 234, 236*a-b*, 238, 240*a-b*, 242*a-c*, 244*a-c*, 260, 270, 270-1 may be similar in configuration and/or functionality to similarly named and/or numbered components as described herein. In some embodiments, the system 200 (and/or portions thereof) may comprise an AR/AI-based 3D human body modeling program, system, and/or platform programmed and/or otherwise configured to execute, conduct, and/or facilitate the methods 400, 700 of FIG. 4 and/or FIG. 7 herein, and/or portions or combinations thereof.

III. AR and AI-Constructed 3D Human Body Modeling Interfaces

Turning now to FIG. 3A, FIG. 3B, FIG. 3C, FIG. 3D, FIG. 3E, FIG. 3F, FIG. 3G, FIG. 3H, FIG. 3I, FIG. 3J, and FIG. 3K, diagrams of an example AR output system 300 according to some embodiments are shown. In some embodiments, the example AR output system 300 may comprise different versions or instances of an interface 320*a-k* output in an AR manner, e.g., via an AR device (not separately shown), such as the AR device 130, 230 of FIG. 1 and/or FIG. 2 herein. In some embodiments, instances of the interface 320*a-k* may comprise one or more instances or versions of a web page, web form, database entry form, Application Programming Interface (API), spreadsheet, table, map interface, MR or AR input/output, and/or application or other GUI via which data is input and/or output. The instances of the interface 320*a-k* may, for example, comprise a front-end of an AR and AI-facilitated or enabled 3D human body modeling program and/or platform programmed and/or otherwise configured to execute, conduct, and/or facilitate the methods 400, 700 of FIG. 4 and/or FIG. 7 herein, and/or portions or combinations thereof. In some embodiments, the instances of the interface 320*a-k* may be output via a computerized device, such as the one or more of the controller device/server 110, 210, the AR devices 130, 230, and/or the apparatus 510 of FIG. 1, FIG. 2, and/or FIG. 5 herein. According to some embodiments, the instances of the interface 320*a-k* may be output via (and are accordingly at least partial representations of) a see-through display device of an AR device and/or display thereof (not shown).

In some embodiments, any or all of the example instances of the interface 320*a-k* may be output based on acquired data that is descriptive of a real-world environment 370 which itself comprises and/or defines a plurality of particular locations 370-1. According to some embodiments, and with reference to FIG. 3A, a first instance of the interface 320*a* may comprise, define, and/or depict various interface elements, such as a disk, stand, or base element 320-1 and/or a prompt or instruction element 320-2. As depicted, the virtual interface elements, such as the base element 320-1 and the instruction element 320-2, may be projected and/or output to coincide with a specific/particular location 370-1. The particular location 370-1 may comprise a default location based on the FoV represented by the first instance of the interface 320a, for example, and/or may be set, defined, and/or adjusted by the user/wearer (not shown) and/or may be dynamically placed (e.g., by execution of an AI and/or AR logic routine) to coincide with an unobstructed, flat, and/or floor area (e.g., as depicted) of the environment 370. In some embodiments, the user-wearer may provide input (e.g., as directed by the instruction element 320-2) to define one or more parameters of the first instance of the interface 320a (and/or of the system 300). The user may conduct a hand gesture, such as a pinch and expand motion, for example, to define an area about the particular location 370-1 where the AR projection is desired to be generated/situated.

Figure 3A:
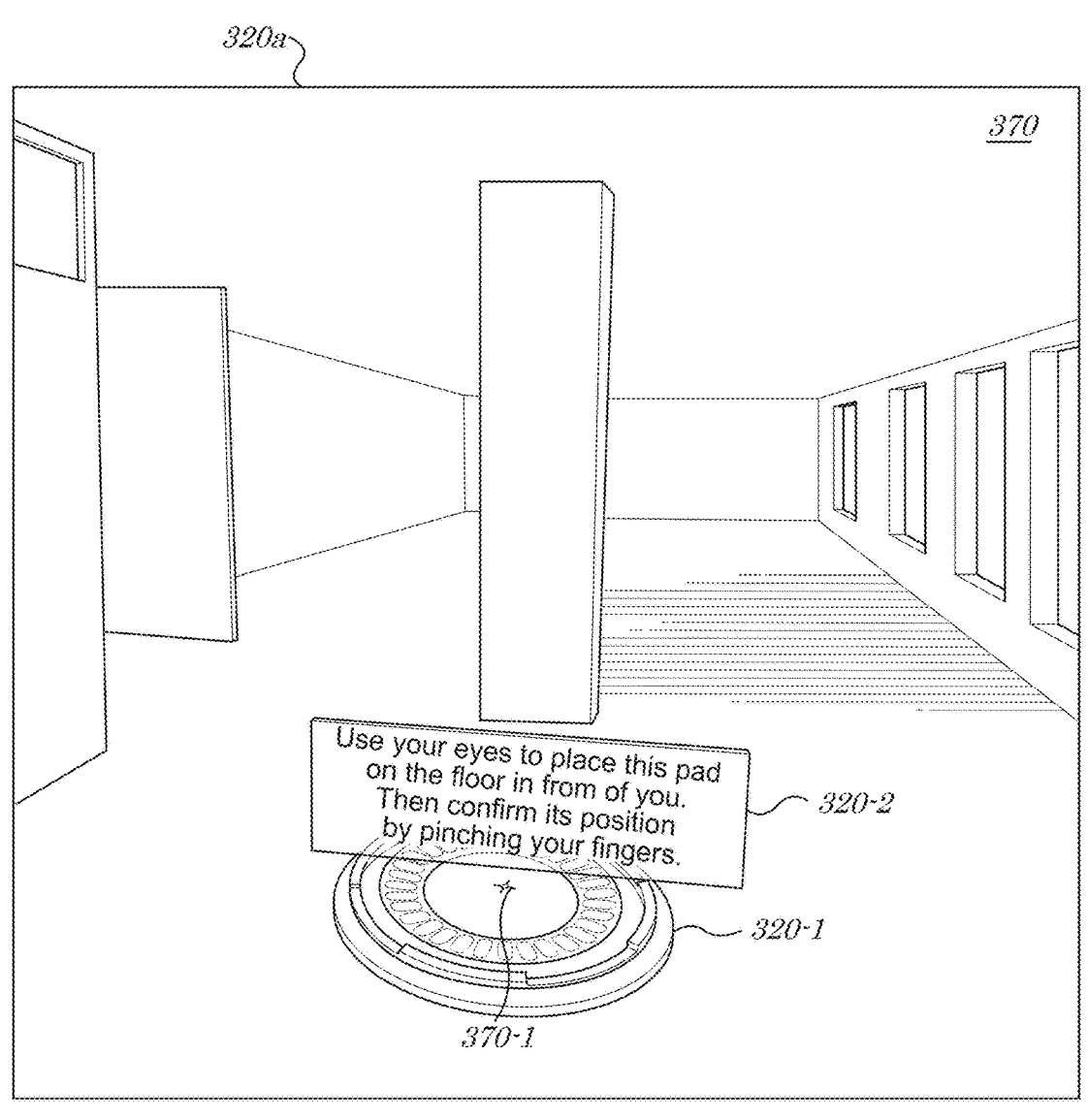
Figure 3B:
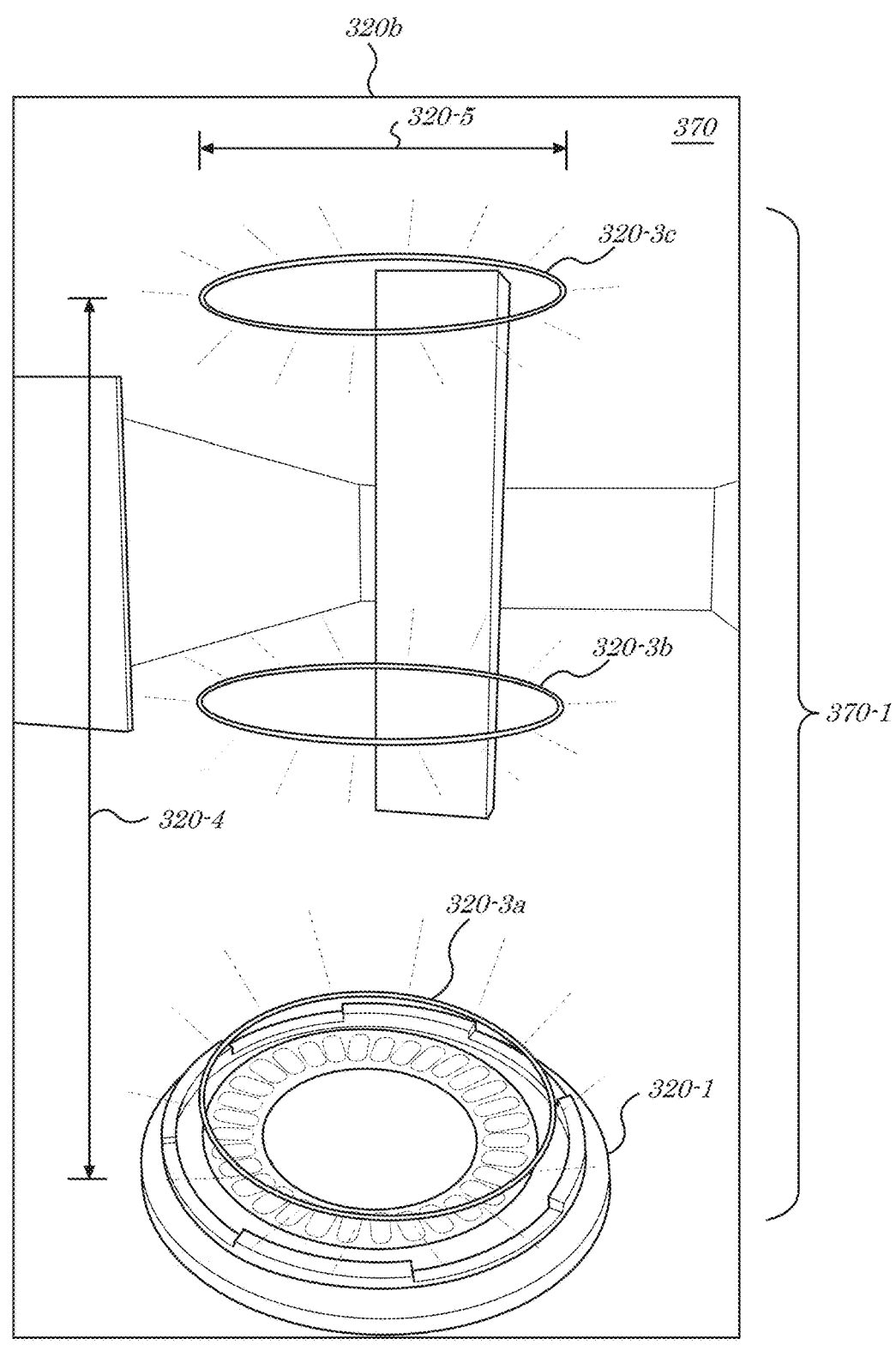

According to some embodiments, and with reference to FIG. 3B, a second instance of the interface 320b may comprise, define, and/or depict a plurality of volume elements 320-3a, 320-3b, 320-3c that represent the extents of a volume in the environment 370 into which an AR projection is to be located. The volume elements 320-3a, 320-3b, 320-3c may represent and/or correspond to, for example, an overall height 320-4 and/or diameter 320-5 (or width and depth in a case where the volume is not cylindrical as it is on the non-limiting example shown) of the AR projection space or volume. In some embodiments, this 3D space (e.g., defined by the height 320-4 and diameter 320-5 and/or with respect to the particular location 370-1) may be defined by the user/wearer (e.g., via input therefrom) and/or automatically defined, e.g., based on medical record data for a particular individual. The height 320-4 and diameter 320-5 may be automatically defined and/or selected, for example, to define the volume such that it is large enough to fit the known and/or computed dimensions of the particular individual, e.g., as virtually rendered in the environment 370. According to some embodiments, the particular location 370-1 may comprise a point, line, or area, e.g., as in FIG. 3A or may comprise a volume (e.g., as defined and/or represented by the volume elements 320-3a, 320-3b, 320-3c) as in FIG. 3B, where the particular individual is to be virtually rendered, projected, and/or output.

Figure 3C:
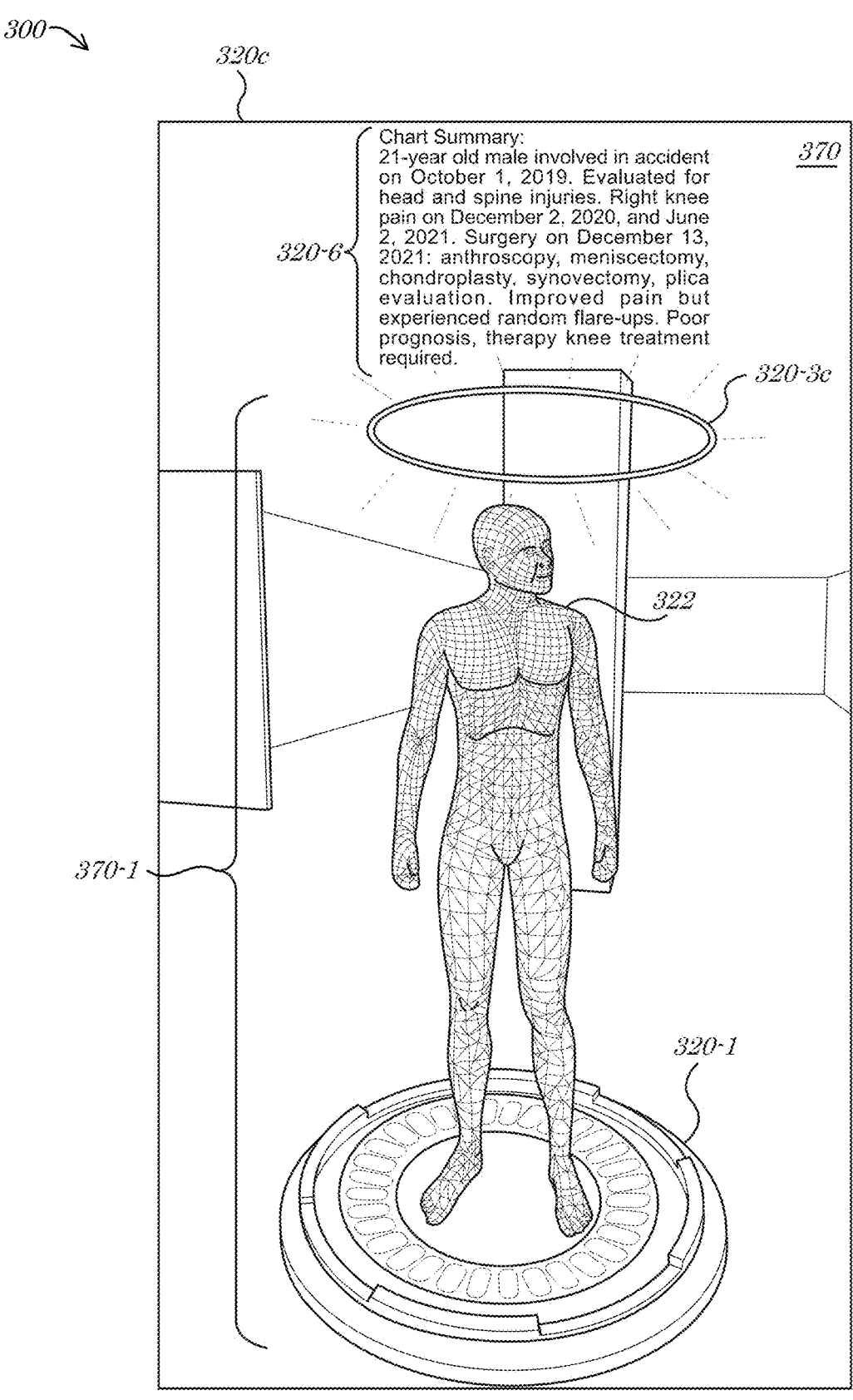

In some embodiments, and with reference to FIG. 3C, a third instance of the interface 320c may comprise a 3D human body model 322 disposed at the particular location 370-1, e.g., between the base element 320-1 (e.g., "standing" thereon) and an upper volume element 320-3c. The 3D human body model 322 may, for example, be sized, shaped, and/or configured (e.g., male, female) based on 3D human body model data stored in a data structure (not shown) accessible to (and/or part of) the system 300. According to some embodiments, as described herein, the data structure may be constructed and/or populated by an LLM that operates upon medical records, e.g., to parse out and/or identify medical event data related to various body parts of the individual. In some embodiments, the medical record data may be summarized and output via a medical summary element 320-6 output adjacent to (e.g., above, as depicted in FIG. 3C) the 3D human body model 322.

Figure 3D:
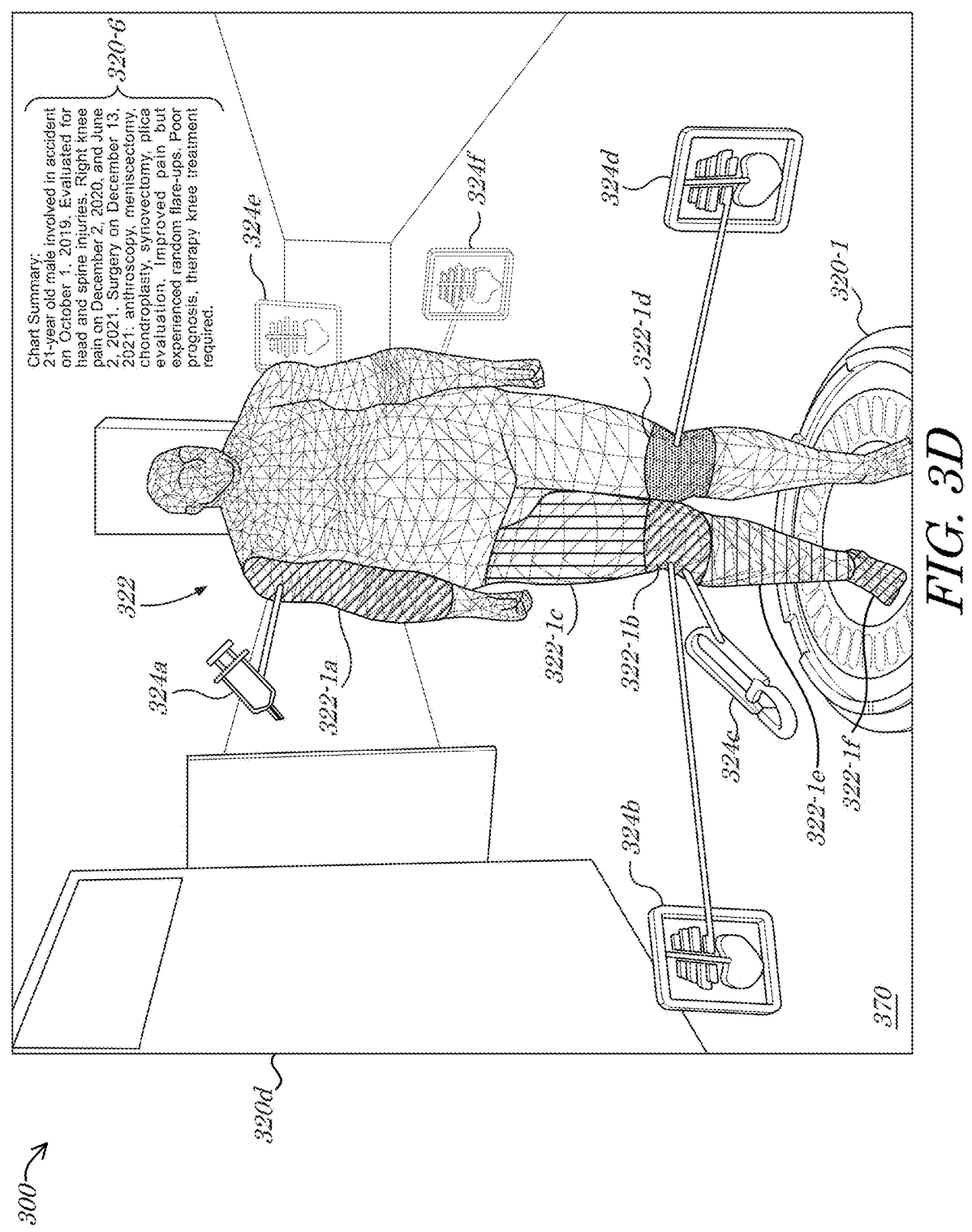

According to some embodiments, and with reference to FIG. 3D, a fourth instance of the interface 320d may comprise a rendering of the 3D human body model 322 (e.g., with different body proportions than those depicted in FIG.

3C) disposed at the particular location 370-1, e.g., upon the base element 320-1. In some embodiments, the fourth instance of the interface 320d may comprise the medical summary element 320-6 output near the 3D human body model 322, e.g., providing an AI-generated summary of a medical history of the modeled individual. According to some embodiments, different portions of the 3D human body model 322 that correspond to different body parts of the individual may be indicated (e.g., utilizing thicker rendering line weights, different colors, patterns, etc.) and/or may be individually selectable (e.g., comprise different input elements). As depicted in FIG. 3D for purposes of non-limiting example, the 3D human body model 322 comprises and/or defines a first or right arm portion 322-1a, a second or right knee portion 322-1b, a third or right thigh portion 322-1c, a fourth or left knee portion 322-1d, a fifth or right shin portion 322-1e, and/or a sixth or right foot portion 322-1f. In some embodiments, one or more medical event icons 324a-f may be output with an indication of which particular body part the medical event icons 324a-f relate to (e.g., with line leaders as shown).

In some embodiments, the medical event icons 324a-f may be output with different sizes, colors, shapes, animations, etc., to indicate different types, levels of importance, temporal aspects, and/or other attributes of the medical event data embedded in or with respect to the particular related portion of the 3D human body model 322. As depicted solely for purposes of non-limiting example in FIG. 3D, for example, a first medical event icon 324a may comprise a graphical representation of a syringe (e.g., indicating an injection), a second medical event icon 324b may comprise a graphical representation of a medical record file or event (e.g., indicating that medical data of some sort exists), a third medical event icon 324c may comprise a graphical representation of a scalpel (e.g., indicating that an operation occurred), and/or fourth, fifth, and sixth medical event icons 324d-f may comprise graphical representations of medical record files or events (e.g., indicating that medical data of some sort exists). As depicted in FIG. 3D, the first medical event icon 324a may be tied or linked to and/or represent the right arm portion 322-1a (e.g., corresponding to the right arm of the individual being modeled), the second medical event icon 324b and the third medical event icon 324c may be tied or linked to and/or represent the right knee portion 322-1b (e.g., corresponding to the right knee of the individual being modeled), the fourth medical event icon 324d may be tied or linked to and/or represent the left knee portion 322-1d (e.g., corresponding to the left knee of the individual being modeled), and/or the fifth and sixth medical event icons 324e-f may be tied or linked to and/or represent portions of the 3D human body model 322 that are not visible in FIG. 3D.

In some embodiments, the user/wearer of the AR device with the see-through display via which the fourth instance of the interface 320d may be output, may select one or more of the medical event icons 324a-f and/or one of the corresponding portions 322-1a, 322-1b, 322-1c, 322-1d, 322-1e, 322-1f of the 3D human body model 322 to cause an outputting, transmittal, and/or providing of the embedded/linked/underlying medical data, media, etc. Utilizing a pointer device (not shown), voice commands, eye gaze, movements and/or gestures (e.g., blinking), hand movements and/or gestures, and/or other input objects, for example, the user may select the first medical event icon 324a. According to some embodiments, whether triggered by a selection of one or more of the medical event icons 324a-f or the body portions 322-1a, 322-1b, 322-1c, 322-1d, 322-1e, 322-1f of the 3D human body model 322 of the fourth instance of the interface 320*d* or whether triggered by selection and/or input defining a different type of indicator (not shown) and/or interface element, the user may provide an indication (and the AR device may accordingly receive the indication) of a selection of a particular medical event, data element, and/or body part of the individual. In some embodiments, the selection of the particular medical event, data element, and/or body part of the individual may cause a fifth version of the interface 320*e* as depicted in FIG. 3E to be output. In some embodiments, the fifth version of the interface 320*e* may comprise a portion of the rendering of the 3D human body model 322, e.g., a close-up or zoomed-in version that shows the right arm portion 322-1*a* (e.g., corresponding to the right arm of the individual being modeled) with an adjacent/proximate output of first medical data 344-1*a* corresponding thereto. In such a manner, for example, the user may simply select the right arm portion 322-1*a* and/or the first medical event icon 324*a* to view any or all medical data (e.g., the first medical data 344-1*a*) corresponding thereto.

According to some embodiments, the right arm portion 322-1*a* (and/or any other body portion 322-1*b*, 322-1*c*, 322-1*d*, 322-1*e*, 322-1*f* of the 3D human body model 322) may comprise and/or be defined by various ("virtual") dimensions, e.g., projected into the environment 370. The right arm portion 322-1*a* may comprise and/or be defined, for example, by one or more of a length 326 and a width 328. In some embodiments, the length 326 and the width 328 may be defined by AR and/or AI logic (e.g., by the AR device and/or by a server device) based upon the medical records for the modeled individual. In a case that a full body scan of the individual is available, the model of the individual's body may be utilized to generate, scale, and/or adjust the 3D human body model 322 (and the length 326 and the width 328 thereof). In many cases however, body measurement data within medical records for the individual may be limited to a subset of variables, such as height, weight, gender, and age (or birth date). In some embodiments, the system 300 may evaluate the medical record body data and/or variables and compute the length 326 and the width 328. Given a height and weight of the individual, for example, the system 300 may calculate a Body Mass Index (BMI) for the individual utilizing the following formula "F1":

$$BMI = \frac{\text{Mass}_{kg}}{\text{Height}_m^2} = \frac{\text{Mass}_{lb}}{\text{Height}_{in}^2} \times 703 \qquad (F1)$$

The length 326 and the width 328 may then be computed (e.g., calculated and/or looked-up) based on the calculated BMI. In such a manner, for example, the rendering of the 3D human body model 322 may be proportioned to resemble the actual individual, even without the system 300 having access to precise data measurements for each body part of the individual. According to some embodiments, each body portion 322-1*a*, 322-1*b*, 322-1*c*, 322-1*d*, 322-1*e*, 322-1*f* of the 3D human body model 322 may be proportioned (e.g., by computing respective lengths 326 and widths 328) based on the BMI, height, weight, gender, and/or age of the individual. Different proportional formulas may be employed, for example, depending upon the gender and/or age of the individual, e.g., based on an AI training data set of measurements from other individuals with similar/matching ages and genders. In some embodiments, while a single length 326 and width 328 are depicted for ease of illustration, multiple lengths 326 and widths 328 for any portion/body part may be computed and utilized to generate the 3D human body model 322. The proportional formulas (e.g., based on BMI and/or other metrics) may, for example, define a different width 328 for any number of positions along a length 326 of a body part/portion. In some embodiments, other metrics and/or formulas may be utilized to define the proportions of the 3D human body model 322 (and/or parts thereof) such as, but not limited to, a Body Roundness Indicator (BRI) that utilizes height, weight, and hip circumference (and/or age, gender, etc.) to compute a value between one (1) and twenty (20), with one (1) being a "narrow" body shape and twenty (20) being a "round" body shape. According to some embodiments, such as in the case of the injection indicated by the first medical event icon 324*a*, a specific location indicator "A" may be provided to depict the actual location on the particular body part (e.g., the indicated location on the right arm portion 322-1*a*) where the event occurred.

Figure 3F:
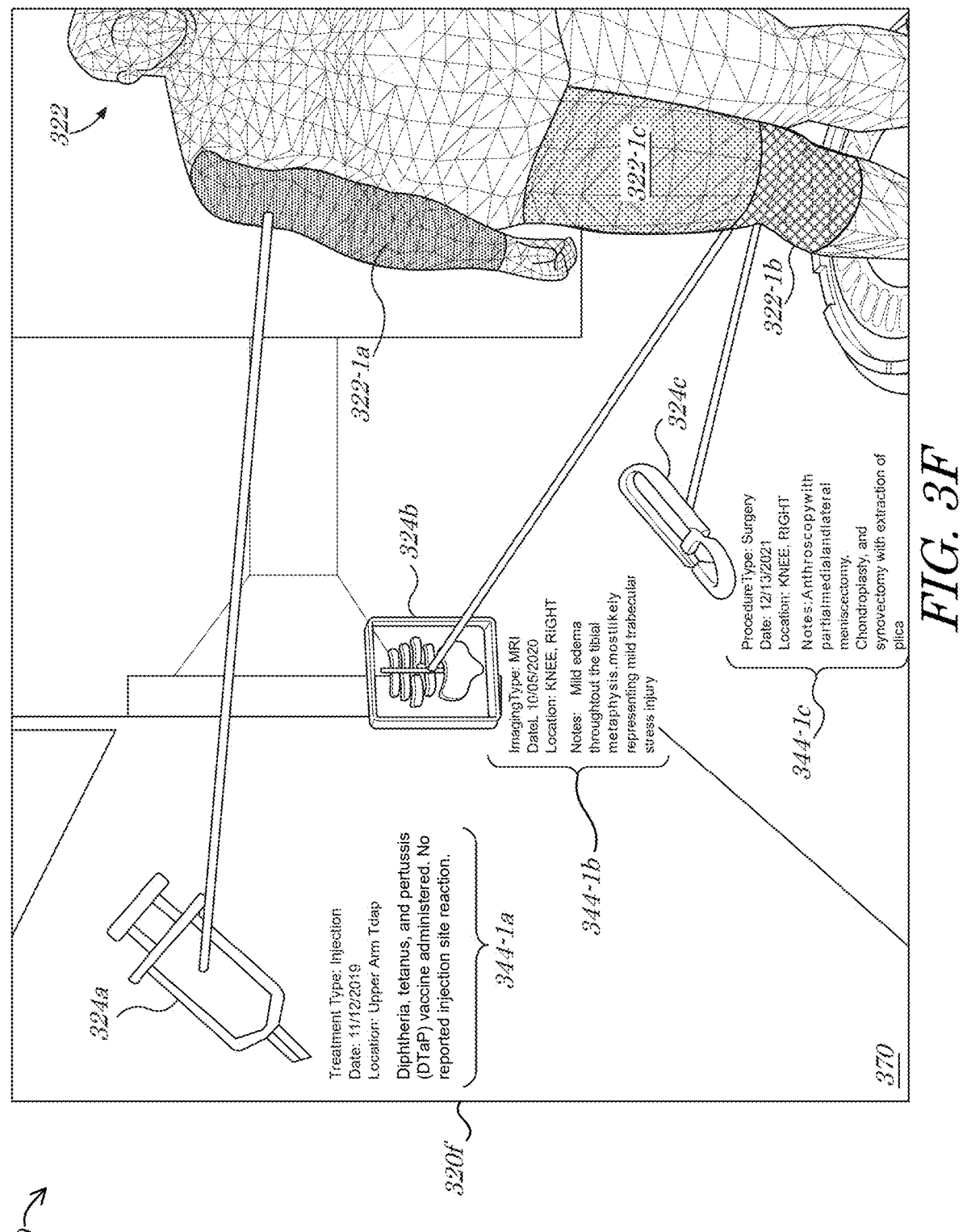

According to some embodiments, and with reference to FIG. 3F, a sixth instance of the interface 320*f* may comprise a portion of the rendering of the 3D human body model 322, e.g., a close-up or zoomed-in version that shows the right arm portion 322-1*a* (e.g., corresponding to the right arm of the individual being modeled) with the adjacent/proximate output of first medical data 344-1*a* corresponding thereto and the right knee portion 322-1*b* (e.g., corresponding to the right knee of the individual being modeled) with adjacent/proximate output of second medical data 344-1*b* and third medical data 344-1*c* corresponding thereto. In such a manner, for example, the user/wearer may select and/or indicate the right knee portion 322-1*b* and be presented with multiple medical data elements relating thereto—e.g., as indicated by the second and third medical event icons 324*b-c* and as detailed by the second and third medical data 344-1*b-c*.

Figure 3G:
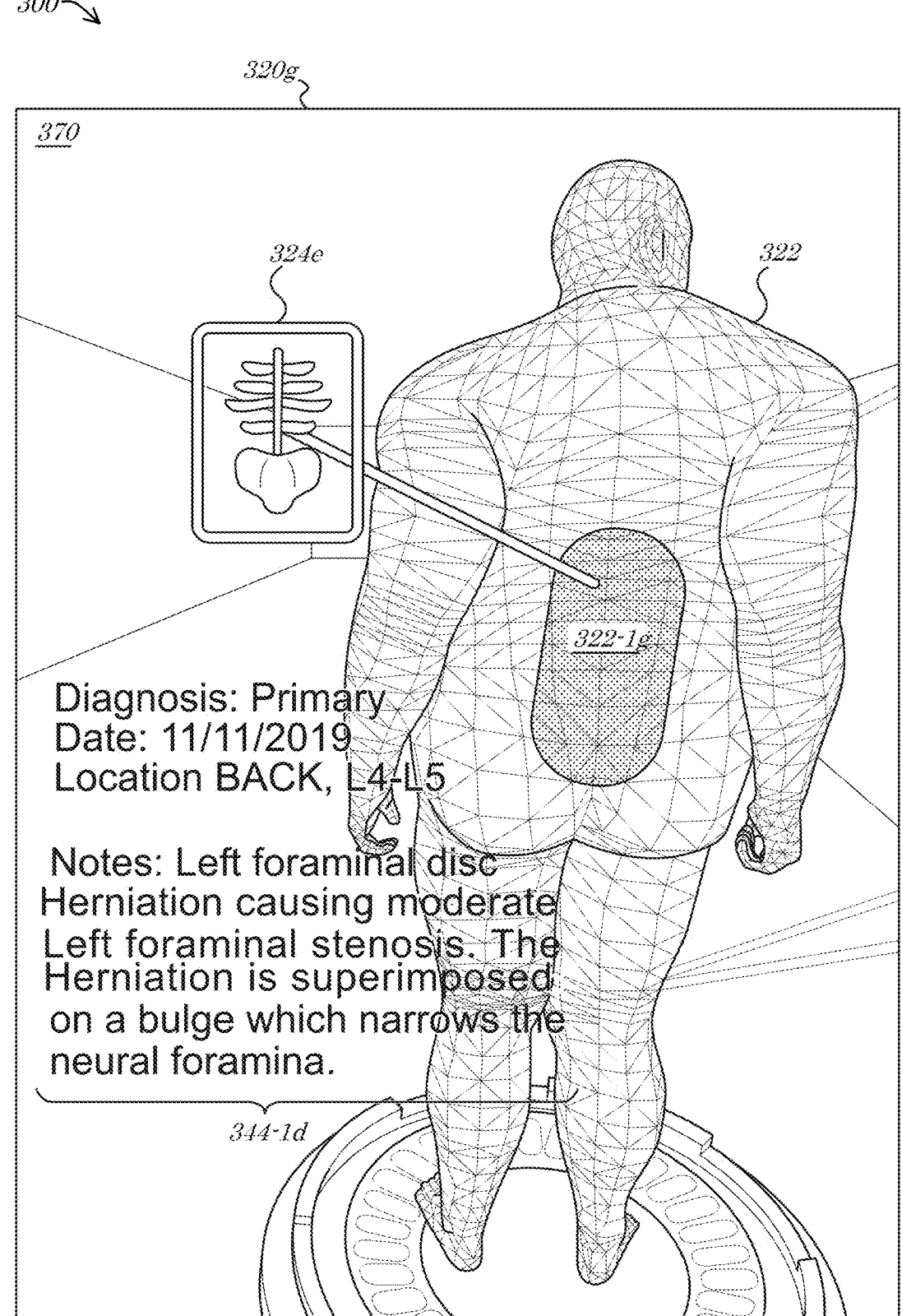

In some embodiments, and with reference to FIG. 3G, a seventh instance of the interface 320*g* may comprise a portion of the rendering of the 3D human body model 322, e.g., a close-up or zoomed-in version that shows a seventh or back (or spine) portion 322-1*g* (e.g., corresponding to the back/spine of the individual being modeled) with an adjacent/proximate output of fourth medical data 344-1*d* corresponding thereto. As depicted in FIG. 3G, the area of the body being investigated and/or tagged with medical data (e.g., the back portion 322-1*g*) may represent an internal portion, area, volume, and/or specific biological component of the individual, such as the spine (or a portion thereof), a bone, ligament, muscle, organ, etc. According to some embodiments, the back portion 322-1*g* may be represented as a portion of a skeletal system (not shown) embedded within the 3D human body model 322. In some embodiments, the 3D human body model 322 may comprise different layers, such as a clothing layer, skin layer, muscle layer, skeletal layer, organ layer, etc., that may each be separately toggled on or off within the interfaces 320*a-k*, e.g., at the direction of the user/wearer. In some embodiments, the toggling or switching between layers may be effectuated by a zoom function such that the displayed/output layer changes as the view is zoomed inward (and/or outward). In such a manner, for example, the user/wearer may select and/or indicate the back portion 322-1*g* and be presented with any medical data elements relating thereto—e.g., as indicated by the fifth medical event icon 324*e* and as detailed by the fourth medical data 344-1*d*.

Figure 3H:
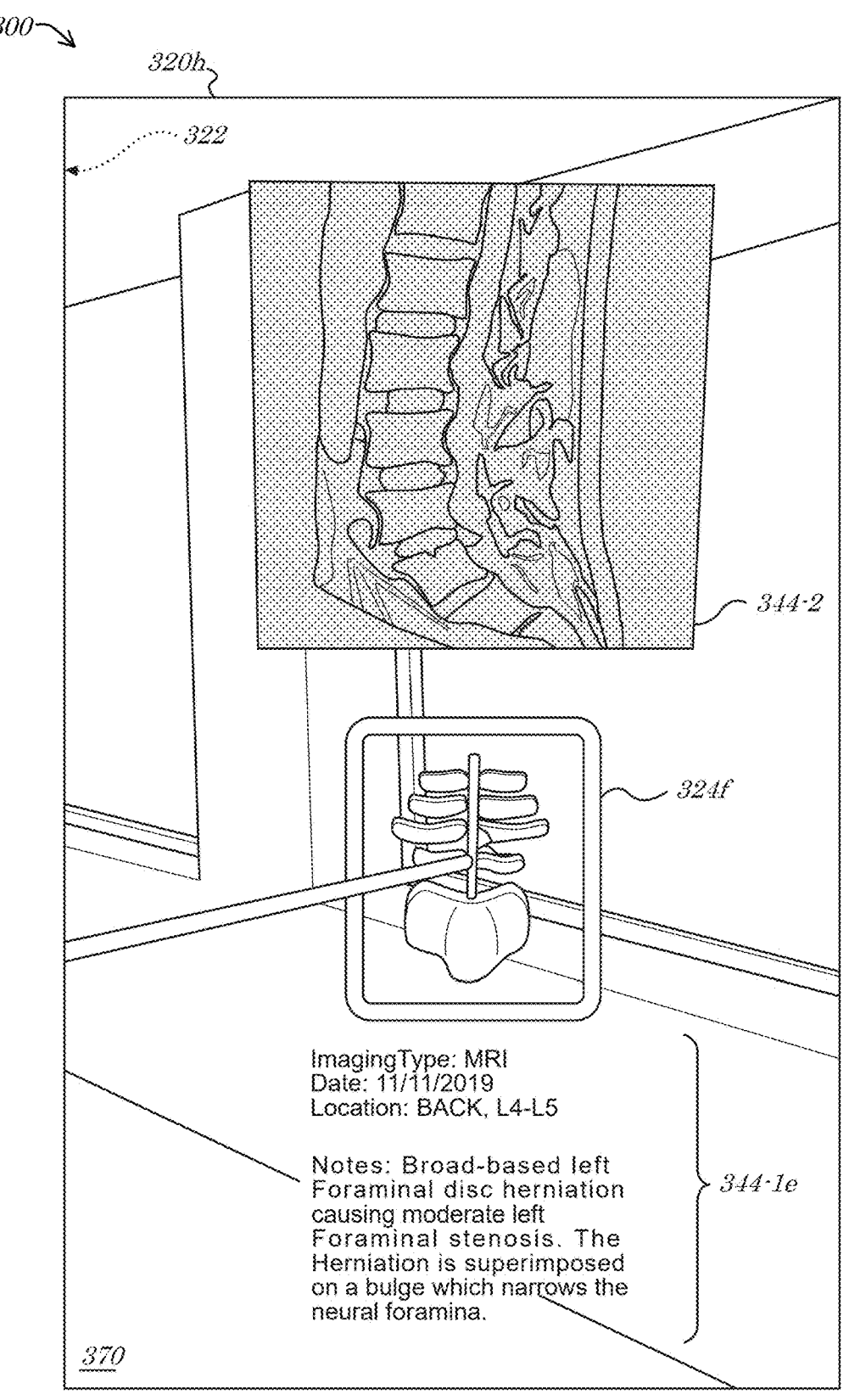

According to some embodiments, and with reference to FIG. 3H, an eighth instance of the interface 320*h* may comprise the sixth medical event icon 324*f* disposed adjacent and/or proximate to the rendering of the 3D human body model 322 (not visible in the view of FIG. 3H) with an adjacent/proximate output of fifth medical data 344-1e corresponding thereto. In some embodiments, the eighth instance of the interface 320h may comprise medical image data 344-2, such as an image and/or video from an X-ray, Magnetic Resonance Imaging (MRI), Computerized Axial Tomography (CAT), and/or other scan of the individual. In such a manner, for example, the user/wearer may select and/or indicate the sixth medical event icon 324f (and/or the corresponding back portion 322-1g) and be presented with the medical image data 344-2. In some embodiments, instead of (or in addition to) the medical image data 344-2 being output adjacent to the 3D human body model 322, the medical image data 344-2 may be output at the same location on (and/or in) the 3D human body model 322 as the corresponding back portion 322-1g. The medical image data 344-2 may be superimposed upon, mapped to, and/or otherwise stitched or coupled to the underlying corresponding back portion 322-1g, for example, e.g., in place of a 3D wire mesh (wireframe) and/or other surface or volume model graphical elements that are generated with the 3D human body model 322.

In some embodiments, the medical image data 344-2 may be utilized to scale, define, and/or adjust one or more portions of the 3D human body model 322. In the case that the medical image data 344-2 is to-scale and/or includes dimensions and/or other physical data, for example, such data/dimensions may be compared to dimensions for corresponding portions of the 3D human body model 322. In the case that a compared portion of the 3D human body model 322 (such as the back portion 322-1g) comprises a dimensional value that differs from a corresponding value indicated by the medical image data 344-2, the portion of the 3D human body model 322 (such as the back portion 322-1g) may be adjusted to match the real-world measured data of the individual. In such a manner, for example, while the overall 3D human body model 322 may be scaled and/or configured based on overall individual height, weight, etc., the 3D human body model 322 and/or portions thereof may be specifically scaled and/or configured to match the best available data. In the example case of the depicted X-ray medical image data 344-2 of a portion of the individual's spine/back, for example, the back portion 322-1g may be sized and/or shaped to match dimensional data from the X-ray medical image data 344-2.

Figure 3I:
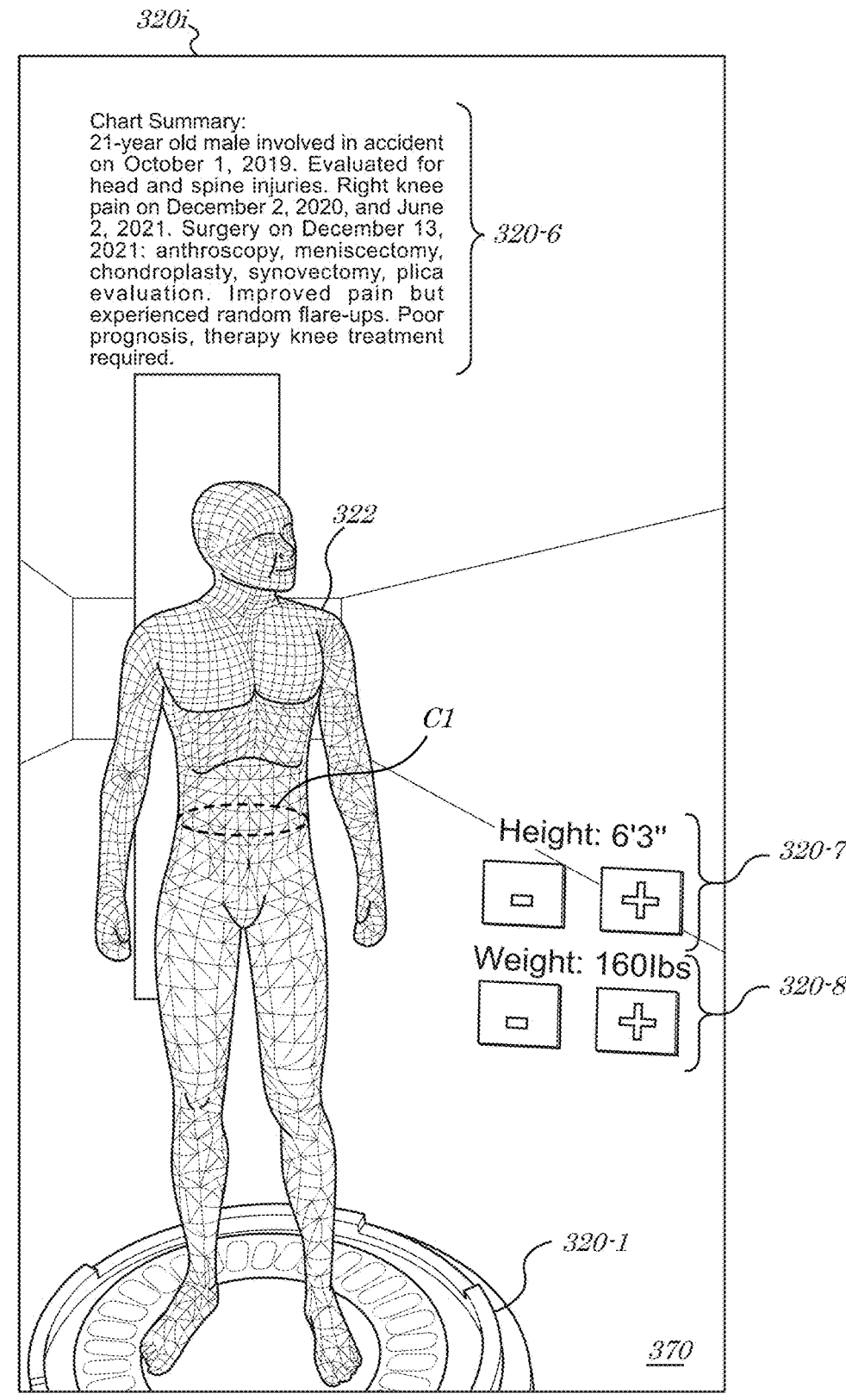

According to some embodiments, and with reference to FIG. 3I, a ninth instance of the interface 320i may comprise the rendering of the 3D human body model 322 (e.g., disposed upon the base element 320-1) with the medical summary element 320-6 output adjacent thereto and with a height element 320-7 and/or a weight element 320-8. In some embodiments, the height element 320-7 and weight element 320-8 may output/display the current height and weight, respectively, of the individual being modeled. In some embodiments, as shown in FIG. 3I, the height element 320-7 and weight element 320-8 may each comprise input mechanisms (such as the depicted plus and minus buttons) that permit or enable the user/wearer to adjust the height and weight, respectively, utilized by the system 300 to generate the 3D human body model 322. According to some embodiments, the user-defined height and weight (as indicated and/or adjusted by the height element 320-7 and weight element 320-8) may be utilized to automatically scale the various portions of the 3D human body model 322. The BMI for the modeled individual represented in FIG. 3I at a height of six feet, three inches (6'3") and a weight of one hundred sixty pounds (160-lb) is twenty (20), for example, and a first girth "C1" may be calculated and utilized to render the torso of the 3D human body model 322 as depicted FIG. 3I. According to some embodiments, such as in a case where the height and weight parameters are changed as depicted in a tenth instance of the interface 320j shown in FIG. 3J to a height of four feet, six inches (4'6") and a weight of eighty pounds (80-lb), the BMI is nineteen and three tenths (19.3). In some embodiments, a second girth "C2" may be calculated and utilized to render the torso of the 3D human body model 322 as depicted FIG. 3J. According to some embodiments, even though the height and weight have changed significantly between the two versions of the 3D human body model 322 in the ninth instance of the interface 320i and the tenth instance of the interface 320j, as the BMI values are quite similar (e.g., within a predefined range or band) the values of the two girths "C1" and "C2" may be substantially equivalent as well.

Figure 3J:
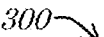
Figure 3J:
Figure 3K:
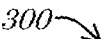

In some embodiments, the tenth instance of the interface 320j may comprise a menu 320-9 that the user/wearer may manipulate and/or interact with utilizing their hand "B", as shown in FIG. 3J. According to some embodiments, and as depicted with respect to an eleventh instance of the interface 320k shown in FIG. 3K, the menu 320-9 may provide an option to utilize and/or the system 300 may otherwise output a web interface 320-10. In such a manner, for example, the user may view and/or interact with the 3D human body model 322 (e.g., to analyze a health history and/or condition of the individual being modeled) and simultaneously navigate to and interact with various web-based menus, pages, applications, tools, etc., by utilizing their hand "B" (and/or other input mechanisms not separately shown) to provide input via the web interface 320-10. The user may utilize the web interface 320-10, for example, to interact with a web-based insurance claim adjustment and/or evaluation tool while they are gathering data regarding the individual from the 3D human body model 322.

While various components of the example instances of the interface 320a-k have been depicted with respect to certain labels, layouts, headings, titles, graphical elements, and/or configurations, these features have been presented for reference and example only. Other labels, layouts, headings, titles, graphical elements, and/or configurations may be implemented without deviating from the scope of embodiments herein. Similarly, while a certain number of tabs, information screens, form fields, and/or data entry options have been presented, variations thereof may be practiced in accordance with some embodiments. In some embodiments, the data output by the example instances of the interface 320a-k may be provided in a temporal context. The user/wearer may be able to switch from data representing a first time to data representing a second time (e.g., via a timeline interface, not separately shown), for example, such as to view a progression of medical events that have occurred with respect to the individual (or a particular body part thereof).

Fewer or more components 320a-k, 320-1, 320-2, 320-3a, 320-3b, 320-3c, 320-4, 320-5, 320-6, 320-7, 320-8, 320-9, 320-10, 322, 322-1a, 322-1b, 322-1c, 322-1d, 322-1e, 322-1f, 322-1g, 324a-f, 326, 328, 344-1a, 344-1b, 344-1c, 344-1d, 344-1e, 344-2, 370, 370-1 and/or various configurations of the depicted components 320a-k, 320-1, 320-2, 320-3a, 320-3b, 320-3c, 320-4, 320-5, 320-6, 320-7, 320-8, 320-9, 320-10, 322, 322-1a, 322-1b, 322-1c, 322-1d, 322-1e, 322-1f, 322-1g, 324a-f, 326, 328, 344-1a, 344-1b, 344-1c, 344-1d, 344-1e, 344-2, 370, 370-1 may be included in the system 300 without deviating from the scope of embodiments described herein. In some embodiments, the components 320*a-k*, 320-1, 320-2, 320-3*a*, 320-3*b*, 320-3*c*, 320-4, 320-5, 320-6, 320-7, 320-8, 320-9, 320-10, 322, 322-1*a*, 322-1*b*, 322-1*c*, 322-1*d*, 322-1*e*, 322-1*f*, 322-1*g*, 324*a-f*, 326, 328, 344-1*a*, 344-1*b*, 344-1*c*, 344-1*d*, 344-1*e*, 344-2, 370, 370-1 may be similar in configuration and/or functionality to similarly named and/or numbered components as described herein. In some embodiments, the system 300 (and/or portions thereof) may comprise an AR/AI-based 3D human body modeling program, system, and/or platform programmed and/or otherwise configured to execute, conduct, and/or facilitate the methods 400, 700 of FIG. 4 and/or FIG. 7 herein, and/or portions or combinations thereof.

IV. AR and AI-Constructed 3D Human Body Modeling Processes

Figure 4:
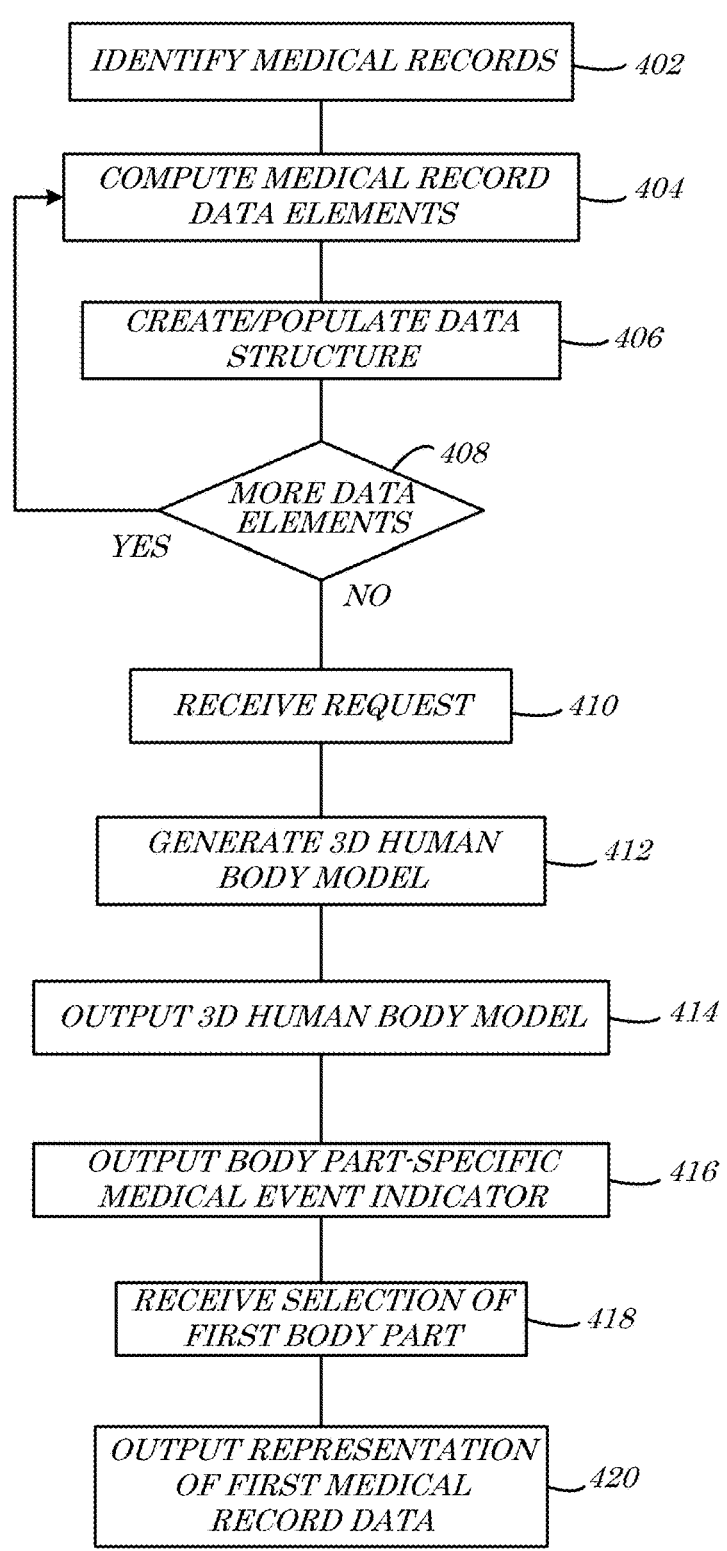
FIG. 4 is a flow diagram of a method according to some embodiments.
Figure 5:
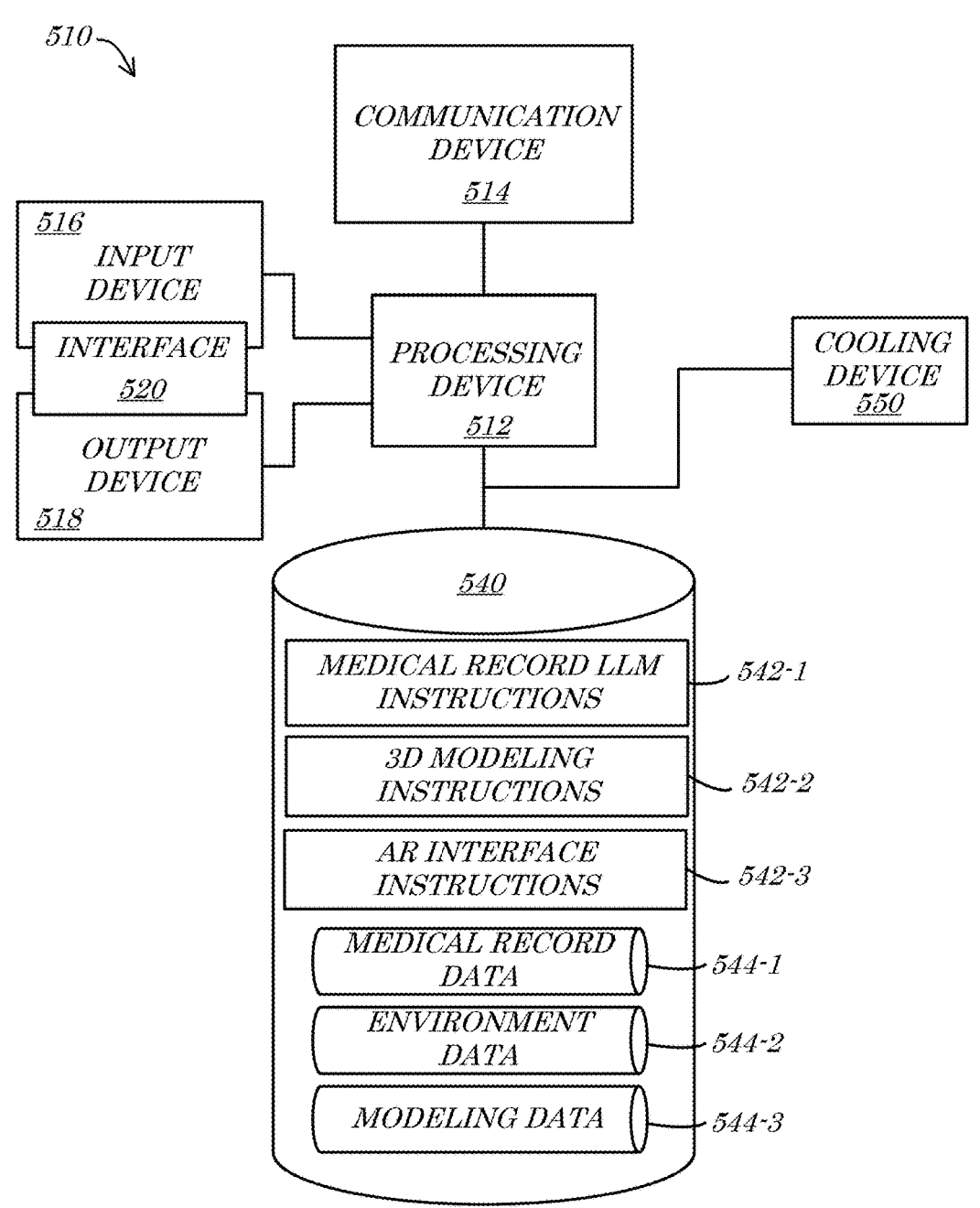
FIG. 5 is a block diagram of an apparatus according to some embodiments.
Figure 6A:
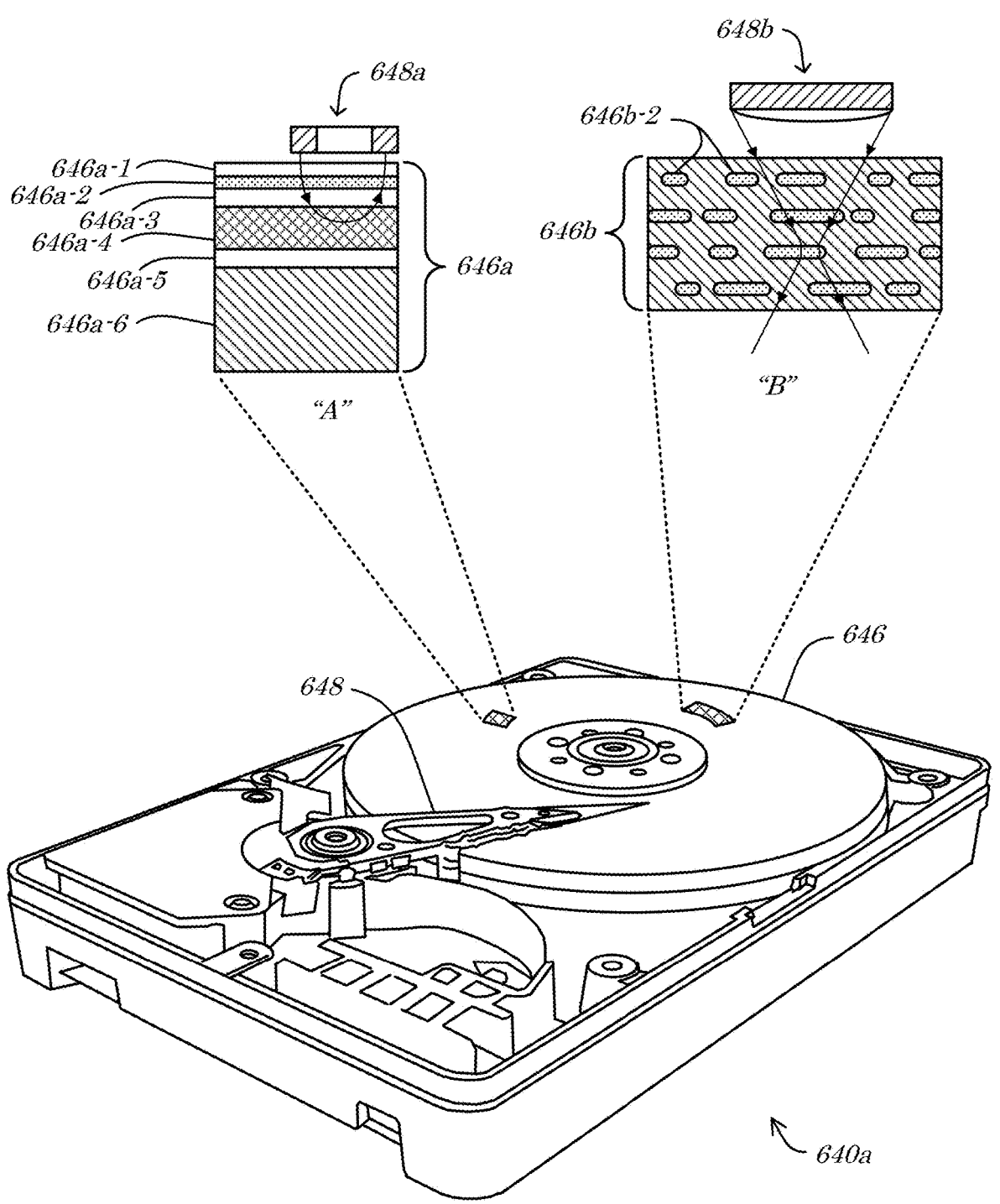
FIG. 6A, FIG. 6B, FIG. 6C, FIG. 6D, and FIG. 6E are perspective diagrams of exemplary data storage devices according to some embodiments.
Figure 6B:
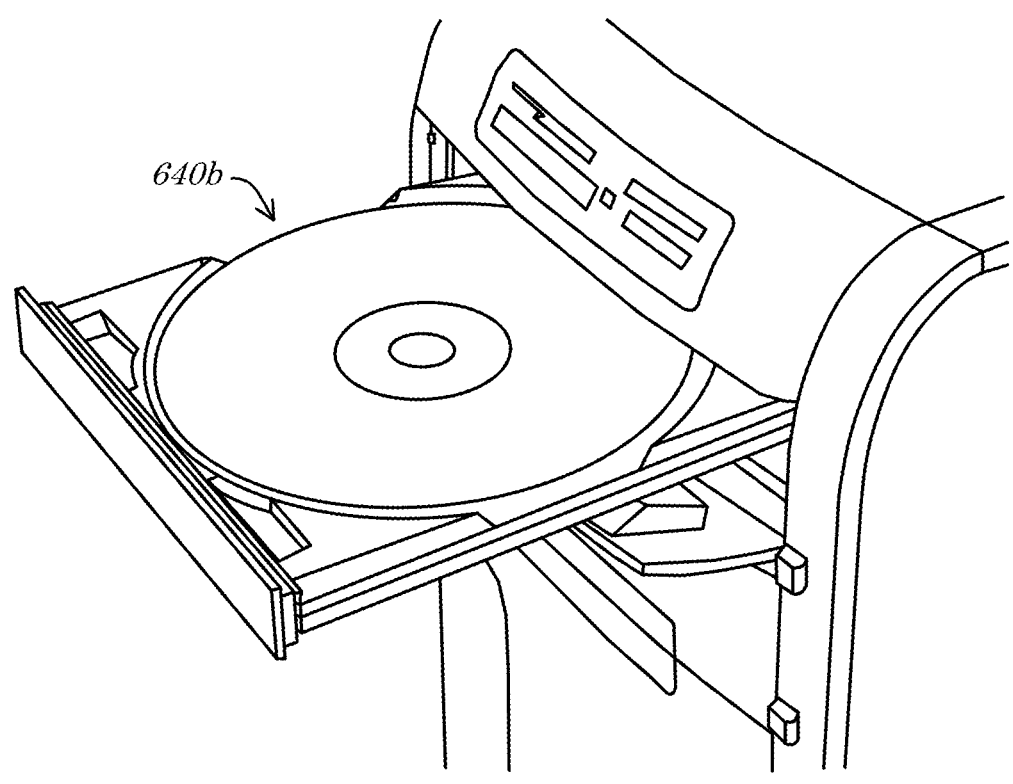
Figure 6C:
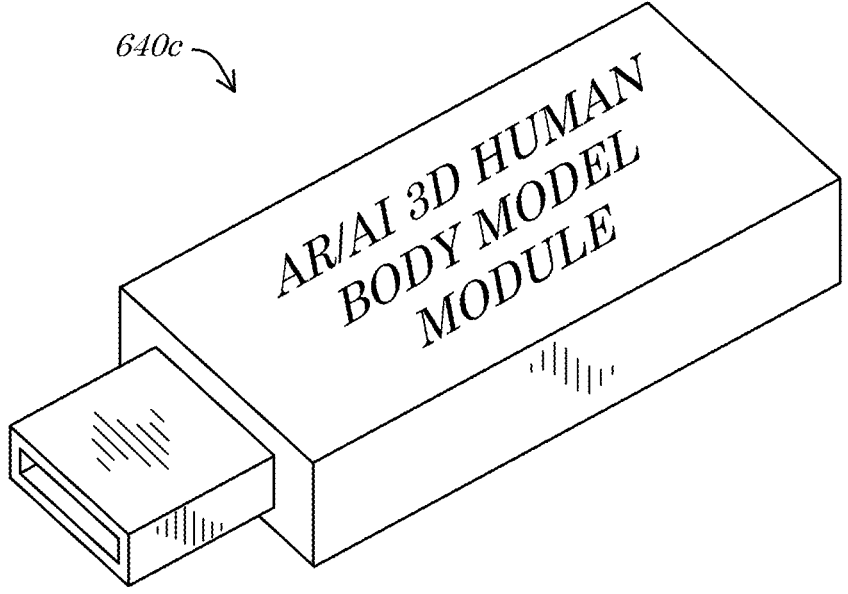
Figure 6D:
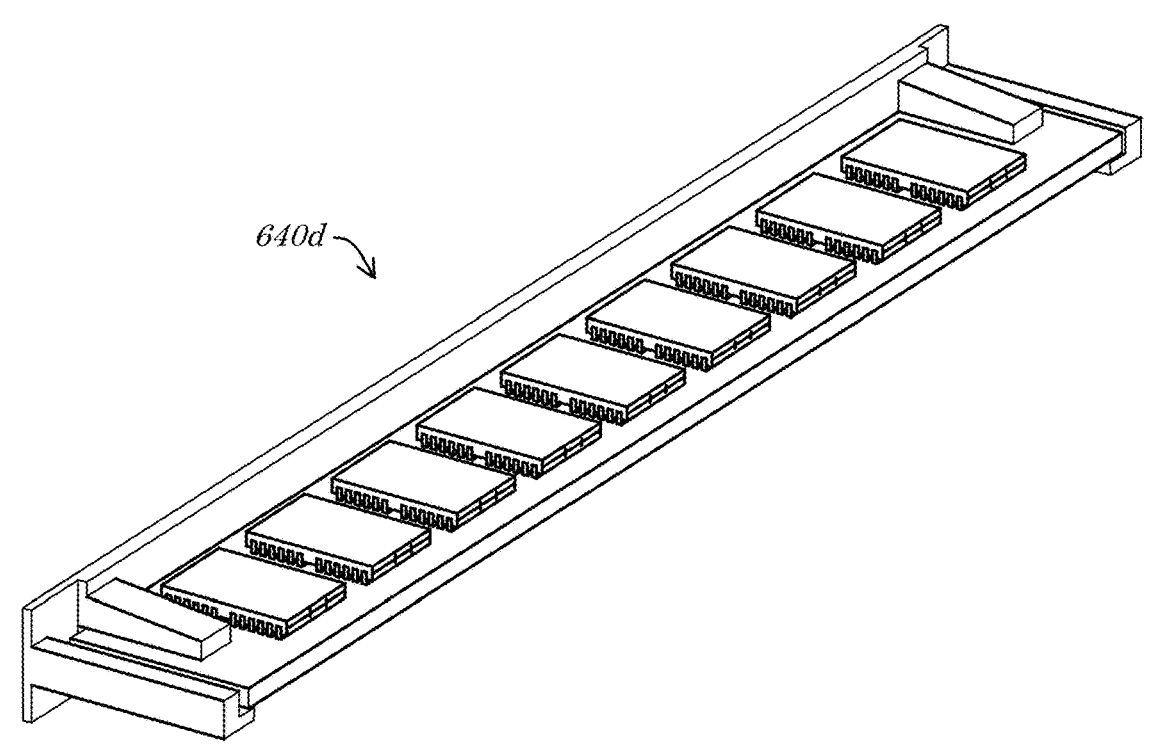
Figure 6E:
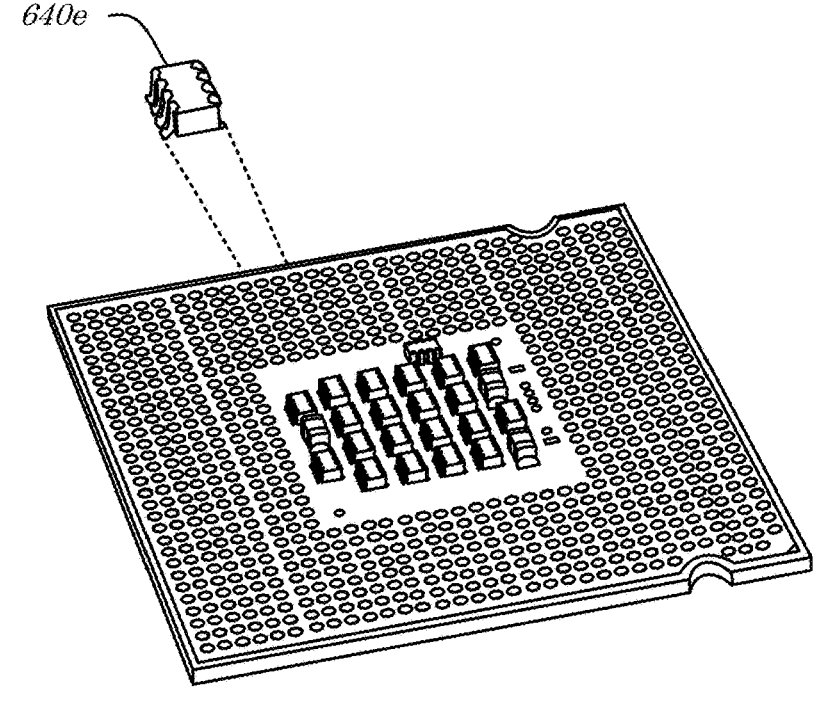

Referring now to FIG. 4, a flow diagram of a method 400 according to some embodiments is shown. In some embodiments, the method 400 may be performed and/or implemented by and/or otherwise associated with one or more specialized and/or specially-programmed computers (e.g., one or more of the controller device/server 110, 210, the AR devices 130, 230 and/or the apparatus 510 of FIG. 1, FIG. 2, and/or FIG. 5 herein), computer terminals, computer servers, computer systems and/or networks, and/or any combinations thereof (e.g., by one or more multi-threaded and/or multi-core processing units of an AR/AI-based 3D human body modeling system). In some embodiments, the method 400 may be embodied in, facilitated by, and/or otherwise associated with various input mechanisms and/or interfaces (such as the interfaces 320*a-k*, 520 of FIG. 3A, FIG. 3B, FIG. 3C, FIG. 3D, FIG. 3E, FIG. 3F, FIG. 3G, FIG. 3I, FIG. 3J, FIG. 3K, and/or FIG. 5 herein).

The process diagrams and flow diagrams described herein do not necessarily imply a fixed order to any depicted actions, steps, and/or procedures, and embodiments may generally be performed in any order that is practicable unless otherwise and specifically noted. While the order of actions, steps, and/or procedures described herein is generally not fixed, in some embodiments, actions, steps, and/or procedures may be specifically performed in the order listed, depicted, and/or described and/or may be performed in response to any previously listed, depicted, and/or described action, step, and/or procedure. Any of the processes and methods described herein may be performed and/or facilitated by hardware, software (including microcode), firmware, or any combination thereof. For example, a storage medium (e.g., a hard disk, Random Access Memory (RAM) device, cache memory device, Universal Serial Bus (USB) mass storage device, and/or Digital Video Disk (DVD); e.g., the memory/data storage devices 140, 240*a-b*, 540, 640*a-e*, 740 of FIG. 1, FIG. 2, FIG. 5, FIG. 6A, FIG. 6B, FIG. 6C, FIG. 6D, FIG. 6E, and/or FIG. 7 herein) may store thereon instructions that when executed by a machine (such as a computerized processor) result in performance according to any one or more of the embodiments described herein.

In some embodiments, the method 400 may comprise identifying (e.g., by an electronic processing device (e.g., of a server device) and/or by executing an LLM) a set of medical records for an individual, at 402. The method 400 may, for example, process stored data in a medical records repository to identify data elements and/or events tagged with and/or belonging to a particular individual (or group of individuals for group-based analysis). According to some embodiments, the data may be searched utilizing an identifier of the individual, such as a name, address, Social Security Number (SSN), and/or a biometric identifier, such as a thumb or fingerprint, facial recognition, retina scan, and/or DNA sample/analysis. According to some embodiments, one or more data sources may be searched to identify, locate, and/or download (e.g., acquire) medical records for the individual. In some embodiments, the identifying and/or acquiring may comprise utilizing credentials to access one or more data sources and/or data storage structures, databases, and/or data storage service provider portals. In some embodiments, the credentials may be received and/or input (e.g., by a user of the system and/or by the individual themselves). According to some embodiments, the medical record data may be from various sources and/or may comprise various formats. The medical record data may be acquired from medical record databases, social media accounts/postings, and/or recorded video, for example, and/or may comprise various document formats, such as PDF, MS® Word™, text files, CSV files, images, videos, JSON files, and/or other unstructured, semi-structured, and/or structured data.

According to some embodiments, the method 400 may comprise computing (e.g., by the electronic processing device and/or by executing the LLM) a plurality of medical record data elements descriptive of discrete medical record events for the individual, at 404. Any or all medical record data for the individual (and/or group) may be analyzed by a medical record LLM trained on historic medical record data, for example. In some embodiments, the medical record LLM may parse and/or summarize the data by identifying and/or extracting dates, procedure types, doctor visits, operations, injections, injuries, therapies, etc. According to some embodiments, the data may be converted into text format for input into the medical record LLM. In some embodiments, a Retrieval-Augmented Generation (RAG) process and/or semantic searching may be utilized to produce LLM output based on the medical record data. According to some embodiments, the medical record data may be searched for physical attribute data of the individual, such as height, weight, BMI, and/or body part-specific measurements (either acquired by manual measurement or from medical device output, such as imagery data).

In some embodiments, the method 400 may comprise creating and/or populating (e.g., by the electronic processing device and/or by executing the LLM) a 3D human body model medical record data structure, at 406. The 3D human body model medical record data structure may be configured, for example, to relate various medical events and/or data to the particular parts of the individual's body that were involved and/or implicated. Body parts may be defined discretely by identifying a particular vertebra, bone, or ligament and/or may be defined more regionally, such as "lower back" or "abdominal", and/or more systemically, such as the vascular system, nervous system, etc. According to some embodiments, the data structure may be constructed and/or configured as part of the method 400. The data structure may be built and/or generated prior to and/or during the data population process, for example, e.g., based upon the identified medical record data for the individual. In some embodiments, the population may comprise storing AI-summarized (e.g., at 404) medical record data that relates specific medical events and/or procedures to one or more specific body parts of the individual. In such a manner, for example, the data structure may be specifically formatted to enable and/or facilitate generation of a 3D human body model by an AR device. In some embodiments, the AI-processed and/or defined data and/or the populated data structure may be transmitted to the AR device and/or made available (e.g., via a communication device and/or network) to the AR device.

According to some embodiments, the method 400 may comprise determining (e.g., by the electronic processing device and/or by executing the LLM) whether there are more data elements, at 408. The system may consult a listing of available and/or identified data elements and/or event data, for example, to determine if any data elements and/or events remain unpopulated and/or unprocessed. In some embodiments, a listing of body parts, areas, and/or anatomical components may be consulted to determine whether any data elements exist with respect to any listed parts and/or components (e.g., of the individual). In the case that one or more data elements and/or events remain unpopulated and/or unprocessed, the method 400 may proceed back to and/or comprise computing additional data elements and/or events, at 404.

In the case that all data elements and/or events have been populated and/or processed, the method 400 may proceed to and/or comprise receiving (e.g., by the electronic processing device, via an electronic communication network, and/or via an AR device and/or interface) a request, at 410. The request may, for example, comprise receiving input comprising a command to generate a 3D human body model representing the individual. In some embodiments, the request may be generated via an interface of the AR device and/or may include an indication of the individual (and/or group) for which the 3D human body model should be generated. According to some embodiments, the request may comprise and/or trigger a downloading of the populated 3D human body model medical record data structure to the AR device (e.g., an AR headset).

In some embodiments, the method 400 may continue to and/or comprise, generating (e.g., by a processing device of an AR device and/or by executing AR and/or AI logic) a 3D human body model, at 412. The 3D human body model representing the individual may be generated, for example, based on the populated data structure (and/or data thereof), e.g., from 406. According to some embodiments, the populated data may be utilized to size, scale, and/or configure a 3D wire mesh or polygon 3D model or virtual structure representing the body of the individual. The 3D human body model may comprise, for example, a 3D wire mesh/polygon avatar of the individual. In some embodiments, a height of the avatar/model may be set based on height data for the individual stored in the data structure (e.g., and derived by the AI LLM from the medical records of the individual). According to some embodiments, different body parts and/or portions of the avatar/model may be sized, shaped, and/or configured based on the populated data. One or more proportional algorithms, rules, and/or logic modules or mathematical models may be executed, for example, utilizing as input various physical data of the individual, such as, but not limited to, height, weight, BMI, gender, and age. The proportional algorithm/rules/logic/models may, in some embodiments, utilize the inputs to compute and/or calculate various dimensions, proportions, and/or characteristics of the 3D human body model/avatar.

According to some embodiments, the avatar/model may comprise and/or define a 3D human body model height and, for each of a plurality of body parts: (ii) a body part length and (iii) a body part width (and/or diameter). In some embodiments, the length and/or width values may vary (e.g., may not be uniform) across different portions of any given body part and/or area. The proportional algorithm/rules/logic/models may define and/or calculate, for example, a value for width, diameter, and/or thickness at each of a plurality of locations along a length of a particular body part, e.g., defining a 3D point cloud (e.g., a plurality of 3D points and/or vertices) and/or "mesh" (e.g., a series of interconnected polygons connecting vertices/points to form a 3D polygonal model) for the model/avatar representing the individual. In some embodiments, the body parts that are modeled/proportioned based on the AI-populated medical data may comprise, but are not limited to, one or more legs, one or more arms, a torso, abdomen, back, neck, thigh, head, feet, and/or hands.

In some embodiments, the computation of the proportions and/or dimensions of the avatar/model may be effectuated by employing a formula/algorithm as may be encoded as in the following example formula "F2":

(F2): //Find your BMI. Provide a Max/Min for each value for that range. Determine current value by calculating pct of current BMI range then multiplying pct by the range.

```
/*
 * BMI Values
 * Underweight = <18.5
 * Normal weight = 18.5-24.9
 * Overweight = 25-29.9
 * Obesity = BMI of 30 or greater
 */
var bmi = (weightPounds / Mathf.Pow(heightInches, 2.0f) * 703;
float minBMI = 16.0f;
float maxBMI = 50.0f;
var values = new Dictionary<string, WeightValues>( );
values.Add("gluteusSize", new WeightValues(0, .3, .6, .75, 1));
values.Add("gluteusWidth", new WeightValues(0, 0, 0, .5, 1));
values.Add("lowerWeight", new WeightValues(0, .4, .6, .75, 1));
values.Add("lowerMuscle", new WeightValues(0, .25, .75, .75, 1));
values.Add("upperWeight", new WeightValues(0, .4, .6, .75, 1));
values.Add("upperMuscle", new WeightValues(0, 25, .75, .75, 1)); //
Might be different for female
values.Add("waist", new WeightValues(0, .2, .6, .8, 1));
values.Add("armWidth", new WeightValues(0, 4, .75, 1, 1));
values.Add("forearmWidth", new WeightValues(0, .3, .6, .6, 1));
values.Add("breastSize", new WeightValues(0, .2, .6, .8, .5));
values.Add("breastCleavage", new WeightValues(.5, .5, .5, .4, .2));
values.Add("belly", new WeightValues(0, .4, .6, .75, 1));
values.Add("neckThickness", new WeightValues(0, .2, .6, .6, 1));
values.Add("legSeparation", new WeightValues(0, 0, .3, .5, 1));
values.Add("muscleTone", new WeightValues(0, .2, .5, .4, 0));
```

In the example coded formula "F2", each body part and/or portion that is scaled and/or proportioned may be defined by an array of scaling values where each value may range from zero (0) to one (1). In some embodiments, each of the scaling values may be defined based on the computed BMI for the individual. The computed BMI may be categorized into typical BMI ranges of "underweight", "normal weight", "overweight", and "obese", for example, and each BMI range may define and/or correspond to a modifier (e.g., a multiplier) for any particular body part/portion and/or any particular scaling factor thereof. In some embodiments, such as with respect to the example formula "F2", the individual's BMI value may fall within one of five (5) ranges: (i) below sixteen (16), (ii) between sixteen (16) and eighteen and four tenths (18.4), (iii) between eighteen and one half (18.5) and twenty-four and nine tenths (24.9), (iv) between twenty-four and one half (24.5) and twenty-nine and nine tenths (29.9), and (v) thirty (30) and above. Each range may correspond to a particular scaling factor for each body part/portion such that, for example, an individual with a BMI of fifteen (15) would have a "gluteusSize" (e.g., a variable defining one or more of a length, width, thickness, volume, area, shape, etc., of the individual's gluteus maximus muscle body portion)

scaled by zero (0), where zero (0) is the first value in the array for the "gluteusSize" that accordingly corresponds to the first BMI range. In some embodiments, the scaling factors stored in the array of values may define maximum values for each BMI range. In a case where the individual's BMI is seventeen (17), for example, it would fall into the second BMI range that comprises values extending from sixteen (16) to eighteen and four tenths (18.4), and corresponds to a maximum scaling factor for "gluteusSize" of three tenths (0.3). The spread of BMI values in the second BMI range is two and four tenths (2.4=18.4-16), yielding a proportional value based on the individual's BMI of one (1=17-16) divided by two and four tenths (2.4), which equals four hundred seventeen thousandths (0.417). In some embodiments, this proportionality factor may be multiplied to weight or adjust the maximum scaling factor for the range. For example, the four hundred seventeen thousandths (0.417) proportionality factor may be multiplied by the maximum scaling factor for "gluteusSize" of three tenths (0.3) to define a proportional scaling factor for the particular individual and for the "gluteusSize" parameter of the avatar/model of one hundred twenty-five thousandths (0.125=0.417/0.3). According to some embodiments, the proportional scaling of any particular body part/portion may be non-linear and may be defined by a different formula than the straight proportional weighting example above. The "muscle Tone" attribute of the avatar/model may be scaled lower for lower BMI ranges, for example, may increase for intermediate BMI ranges, and may decrease for the highest BMI range(s); e.g., which may be described and/or defined by a generally parabolic formula or other polynomial equation.

In some embodiments, any source of dimensional data descriptive of the individual may be utilized to proportionally scale the avatar/model and/or different portions and/or parts thereof. The user/wearer of the AR device may provide input to adjust the scaling, for example, and/or scaling may be automatically based upon AI-sourced and/or derived data elements from the individual's medical records. Some dimensional data may be parsed directly from medical record data, such as a height and/or weight of the individual as measured by a nurse at a doctor's visit. In some embodiments, dimensional data may be computed and/or derived from other sources, such as contemporaneous body scans, video footage, and/or via OCR and/or image analysis of medical record image data, such as X-ray, CT, and/or MRI images. According to some embodiments, body parts and/or portions of the model/avatar may be scaled and/or set to specific dimensions. Scaling may be utilized as a default and/or initial generation process, for example, and then any specific data (e.g., measured bicep diameter or pelvic bone dimensions from an X-ray) may be utilized to override, adjust, and/or set specific dimensions for specific body parts/portions, in the case that such more specific data is available. In such a manner, for example, the avatar/model may be generated as an accurate representation of the physical appearance of the individual.

According to some embodiments, the method 400 may comprise outputting (e.g., by the processing device of the AR device and/or by executing the AR and/or AI logic) a representation of the 3D human body model disposed in an AR environment, at 414. The AR environment may comprise, for example, an area proximate to the AR device (and/or user/wearer thereof), such as a real-world area in a FoV of the AR headset. The see-through display device and/or an interface generated, defined, and/or output thereby may, for example, output an indication of the 3D human body model superimposed and/or projected into/onto the real-word area in the FoV. According to some embodiments, the outputting may comprise outputting one or more of a sound, voice, light, light pattern, text, images, video, GUI elements, AR elements, etc. In some embodiments, the AR device may execute AR logic (e.g., a spatial computing and/or 3D environment creation, navigation, and/or rendering program) to generate output in a manner that it appears to the user/wearer as a 3D human-scale model/avatar "standing" in front of the user/wearer. The 3D model may be scaled in accordance with the generation at 412 and/or may be positioned at a particular position, pose, and/or orientation in the AR environment. According to some embodiments, the 3D human body model may be output with an animation, such as an idle animation loop to replicate minor human movements and make the 3D human body model/avatar appear lifelike.

In some embodiments, the method 400 may comprise outputting (e.g., by the processing device of the AR device and/or by executing the AR and/or AI logic) a body part-specific medical event indicator, at 416. The body part-specific medical event indicator may comprise, for example, a representation of a first one of the discrete medical record events for the individual that is mapped to a specific (e.g., first) body part. The system may, for example, indicate the portion of the 3D human body model/avatar to the wearer/user via an AR and/or AR element output via an interface on the see-through display of the AR device. According to some embodiments, the position of the output element on the display may be established by taking into account the eye position(s) of the wearer/user, the location of the AR device and the orientation of the AR device with respect to the position of the device/user in the real-world environment. In some embodiments, as the wearer/user shifts their gaze and/or as the AR device is altered in orientation and/or location, the output element (and/or the model itself) may be dynamically changed or updated to reflect proper positioning (e.g., to continue to appear is if it is superimposed at the location corresponding to the portion of the 3D human body model). In some embodiments, the body part-specific medical event indicator(s) may be interactive, e.g., by comprising and/or defining one or more input elements, areas, and/or volumes in AR space. According to some embodiments, the body part/area/portion mapped to any body part-specific medical event indicator may also or alternatively be output, designated, highlighted, and/or otherwise generated and output to comprise an interactive element.

According to some embodiments, the method 400 may comprise receiving (e.g., by processing device of the AR device and/or via the 3D human body model) an indication of a selection of a first body part, at 418. The user/wearer may, for example, provide input via the 3D human body model (e.g., as an interface and/or via an interface via which it is output) that defines one or more of the first body part and a body part-specific medical event indicator corresponding thereto. The input may be provided and/or defined, in some embodiments, by a definition of focus on the first body part (and/or indicator thereof) such as via tracked eye movement of the user, hand and/or finger gestures of the user, voice commands, and/or pointer-device utilization.

In some embodiments, the method 400 may comprise outputting (e.g., by the processing device of the AR device and/or in response to the selection) a representation of a first one of the plurality of medical record data elements, at 420. The representation may comprise, for example, text, voice, images, and/or multi-media output corresponding to the first one of the discrete medical record events for the individual that is associated with the first body part and is projected/output at an AR location corresponding to the first body part of the individual. According to some embodiments, the output may comprise a text and/or voice summary of one or more medical events that have occurred with respect to the selected/first body part. In some embodiments, the output may comprise an image (and/or video) of a medical procedure, such as an X-ray image, colonoscopy video, etc. According to some embodiments, the image/video may be overlayed onto and/or "stitched" onto the 3D human body model/avatar. In the case of an X-ray image of the individual's left arm, for example, a portion of the 3D human body model/avatar corresponding to the imaged area/volume may be wrapped around and/or inserted into the 3D human body model/avatar, e.g., such that it is visible in place of any default wire mesh, polygon, and/or other 3D model output artifacts.

According to some embodiments, the outputting may also or alternatively comprise outputting a webpage interface, e.g., adjacent and/or proximate to the 3D human body model/avatar within the AR environment. The webpage interface may comprise an interface of an insurance claim evaluation tool, for example, that permits the user to enter (and/or consume) data to (and/or from) a web-based resource while reviewing and/or interacting with the 3D human body model/avatar. In some embodiments, the generation and/or outputting of the 3D human body model/avatar, the various body parts/portions thereof, and/or the body part-specific medical event indicators may be time-specific. The AR interface may comprise a timeline function, for example, where the user may select different historical points in time for which the generated and output AR elements (e.g., the model and indicators) are selected. The time-based generation/outputting may be based, for example, on a time-specific subset of the AI-summarized medical record data for the individual. In such a manner, for example, the user may view and/or interact with different versions of the 3D human body model/avatar in a chronological fashion, e.g., to visualize how the individual's physical and/or medical status has changed over time. According to some embodiments, the user may provide input, such as annotation, notes, and/or conclusions (e.g., claim handling determinations and/or medical diagnosis and/or treatments) that are appended to the medical data stored in relation to the body part-specific medical event indicators (and/or body parts corresponding thereto). In some embodiments, the AR output may be provided in a shared AR environment that is simultaneously output via multiple AR headsets (and/or other devices) such that multiple users may cooperatively and/or simultaneously interact with the 3D human body model/avatar (e.g., a collaborative AR environment).

V. AR and AI-Constructed 3D Human Body Modeling Apparatus, Articles of Manufacture, & Algorithms Turning to FIG. 5, a block diagram of an apparatus 510 according to some embodiments is shown. In some embodiments, the apparatus 510 may be similar in configuration and/or functionality to one or more of the controller device/server 110, 210, the AR devices 130, 230 of FIG. 1 and/or FIG. 2 herein. The apparatus 510 may, for example, execute, process, facilitate, and/or otherwise be associated with the methods 400, 700 of FIG. 4 and/or FIG. 7 herein, and/or portions or combinations thereof. In some embodiments, the apparatus 510 may comprise a processing device 512 (e.g., a processor), a communication device 514, an input device 516, an output device 518, an interface 520, a memory device 540 (storing various programs and/or instructions 542 and data 544), and/or a cooling device 550. According to some embodiments, any or all of the components 512, 514, 516, 518, 520, 540, 542, 544, 550 of the apparatus 510 may be similar in configuration and/or functionality to any similarly named and/or numbered components described herein. Fewer or more components 512, 514, 516, 518, 520, 540, 542, 544, 550 and/or various configurations of the components 512, 514, 516, 518, 520, 540, 542, 544, 550 may be included in the apparatus 510 without deviating from the scope of embodiments described herein.

According to some embodiments, the processor 512 may be or include any type, quantity, and/or configuration of processor that is or becomes known. The processor 512 may comprise, for example, an Intel® IXP 2800 network processor or an Intel® XEON™ Processor coupled with an Intel® E5501 chipset. In some embodiments, the processor 512 may comprise multiple interconnected processors, microprocessors, and/or micro-engines. According to some embodiments, the processor 512 (and/or the apparatus 510 and/or other components thereof) may be supplied power via a power supply (not shown), such as a battery, an Alternating Current (AC) source, a Direct Current (DC) source, an AC/DC adapter, solar cells, and/or an inertial generator. In the case that the apparatus 510 comprises a server, such as a blade server, necessary power may be supplied via a standard AC outlet, power strip, surge protector, and/or Uninterruptible Power Supply (UPS) device.

In some embodiments, the communication device 514 may comprise any type or configuration of communication device that is or becomes known or practicable. The communication device 514 may, for example, comprise a Network Interface Card (NIC), a telephonic device, a cellular network device, a router, a hub, a modem, and/or a communications port or cable. In some embodiments, the communication device 514 may be coupled to receive user input and/or sensor data, e.g., from a user device and/or a sensor device (not shown in FIG. 5). The communication device 514 may, for example, comprise a Bluetooth® Low Energy (BLE) and/or RF receiver device and/or a camera or other imaging device that acquires data from a user (not separately depicted in FIG. 5) and/or a transmitter device that provides the data to a remote server and/or server or communications layer (also not separately shown in FIG. 5). According to some embodiments, the communication device 514 may also or alternatively be coupled to the processor 512. In some embodiments, the communication device 514 may comprise an infrared (IR), RF, Bluetooth™, Near-Field Communication (NFC), and/or Wi-Fi® network device coupled to facilitate communications between the processor 512 and another device (such as a remote server device, not separately shown in FIG. 5).

In some embodiments, the input device 516 and/or the output device 518 are communicatively coupled to the processor 512 (e.g., via wired and/or wireless connections and/or pathways) and they may generally comprise any types or configurations of input and output components and/or devices that are or become known, respectively. The input device 516 may comprise, for example, a keyboard that allows an operator of the apparatus 510 to interface with the apparatus 510 (e.g., by a medical or insurance investigator to perform medical investigations and/or analysis, as described herein). In some embodiments, the input device 516 may comprise a sensor, such as a camera, sound, light, and/or proximity sensor (e.g., of an AR headset system, such as one or more AR pointers and/or hand controls), configured to measure parameter values and report measured values via signals to the apparatus 510 and/or the processor 512. The output device 518 may, according to some embodiments, comprise a display screen and/or other practicable output component and/or device. The output device 518 may, for example, provide an interface (such as the interfaces 320*a-k*, 520 of FIG. 3A, FIG. 3B, FIG. 3C, FIG. 3D, FIG. 3E, FIG. 3F, FIG. 3G, FIG. 3I, FIG. 3J, FIG. 3K, and/or FIG. 5 herein) via which functionality for AR/AI-based 3D human body modeling analysis is provided to a user (e.g., via a website and/or mobile device application). According to some embodiments, the input device 516 and/or the output device 518 may comprise and/or be embodied in a single device, such as a touch-screen monitor.

The memory device 540 may comprise any appropriate information storage device that is or becomes known or available, including, but not limited to, units and/or combinations of magnetic storage devices (e.g., a hard disk drive), optical storage devices, and/or semiconductor memory devices, such as RAM devices, Read Only Memory (ROM) devices, Single Data Rate Random Access Memory (SDR-RAM), Double Data Rate Random Access Memory (DDR-RAM), and/or Programmable Read Only Memory (PROM). The memory device 540 may, according to some embodiments, store one or more of medical record LLM instructions 542-1, 3D modeling instructions 542-2, AR interface instructions 542-3, medical record data 544-1, environment data 544-2, and/or modeling data 544-3. In some embodiments, the medical record LLM instructions 542-1, 3D modeling instructions 542-2, AR interface instructions 542-3, medical record data 544-1, environment data 544-2, and/or modeling data 544-3 may be utilized by the processor 512 to provide output information via the output device 518 and/or the communication device 514.

According to some embodiments, the medical record LLM instructions 542-1 may be operable to cause the processor 512 to process the medical record data 544-1, environment data 544-2, and/or modeling data 544-3 in accordance with embodiments as described herein. Medical record data 544-1, environment data 544-2, and/or modeling data 544-3 received via the input device 516 and/or the communication device 514 may, for example, be analyzed, sorted, filtered, decoded, decompressed, ranked, scored, plotted, and/or otherwise processed by the processor 512 in accordance with the medical record LLM instructions 542-1. In some embodiments, medical record data 544-1, environment data 544-2, and/or modeling data 544-3 may be fed by the processor 512 through one or more mathematical and/or statistical formulas and/or models in accordance with the medical record LLM instructions 542-1 to identify medical records of an individual, parse and/or summarize the records, and create and/or populate a body part-specific data store of summarized/processed medical record data, as described herein.

In some embodiments, the 3D modeling instructions 542-2 may be operable to cause the processor 512 to process the medical record data 544-1, environment data 544-2, and/or modeling data 544-3 in accordance with embodiments as described herein. Medical record data 544-1, environment data 544-2, and/or modeling data 544-3 received via the input device 516 and/or the communication device 514 may, for example, be analyzed, sorted, filtered, decoded, decompressed, ranked, scored, plotted, and/or otherwise processed by the processor 512 in accordance with the 3D modeling instructions 542-2. In some embodiments, medical record data 544-1, environment data 544-2, and/or modeling data 544-3 may be fed by the processor 512 through one or more mathematical and/or statistical formulas and/or models in accordance with the 3D modeling instructions 542-2 to generate and output a 3D human body model sized, shaped, and/or configured to represent the individual, as described herein.

According to some embodiments, the AR interface instructions 542-3 may be operable to cause the processor 512 to process the medical record data 544-1, environment data 544-2, and/or modeling data 544-3 in accordance with embodiments as described herein. Medical record data 544-1, environment data 544-2, and/or modeling data 544-3 received via the input device 516 and/or the communication device 514 may, for example, be analyzed, sorted, filtered, decoded, decompressed, ranked, scored, plotted, and/or otherwise processed by the processor 512 in accordance with the AR interface instructions 542-3. In some embodiments, medical record data 544-1, environment data 544-2, and/or modeling data 544-3 may be fed by the processor 512 through one or more mathematical and/or statistical formulas and/or models in accordance with the AR interface instructions 542-3 to provide interactive input/output functionality for a user/viewer of the 3D human body model such as by permitting selection of body part-specific interactive medical record data elements, as described herein.

According to some embodiments, the apparatus 510 may comprise the cooling device 550. According to some embodiments, the cooling device 550 may be coupled (physically, thermally, and/or electrically) to the processor 512 and/or to the memory device 540. The cooling device 550 may, for example, comprise a fan, heat sink, heat pipe, radiator, cold plate, and/or other cooling component or device or combinations thereof, configured to remove heat from portions or components of the apparatus 510.

Any or all of the exemplary instructions and data types described herein and other practicable types of data may be stored in any number, type, and/or configuration of memory devices that is or becomes known. The memory device 540 may, for example, comprise one or more data tables or files, databases, table spaces, registers, and/or other storage structures. In some embodiments, multiple databases and/or storage structures (and/or multiple memory devices 540) may be utilized to store information associated with the apparatus 510. According to some embodiments, the memory device 540 may be incorporated into and/or otherwise coupled to the apparatus 510 (e.g., as shown) or may simply be accessible to the apparatus 510 (e.g., externally located and/or situated).

Referring to FIG. 6A, FIG. 6B, FIG. 6C, FIG. 6D, and FIG. 6E, perspective diagrams of exemplary data storage devices 640*a-e* according to some embodiments are shown. The data storage devices 640*a-e* may, for example, be utilized to store instructions and/or data, such as the medical record LLM instructions 542-1, 3D modeling instructions 542-2, AR interface instructions 542-3, medical record data 544-1, environment data 544-2, and/or modeling data 544-3, each of which is presented in reference to FIG. 5 herein. In some embodiments, instructions stored on the data storage devices 640*a-e* may, when executed by a processor, cause the implementation of and/or facilitate the methods 400, 700 of FIG. 4 and/or FIG. 7 herein, and/or portions or combinations thereof.

According to some embodiments, the first data storage device 640*a* may comprise one or more various types of internal and/or external hard drives. The first data storage device 640*a* may, for example, comprise a data storage medium 646 that is read, interrogated, and/or otherwise communicatively coupled to and/or via a disk reading device 648. In some embodiments, the first data storage device 640*a* and/or the data storage medium 646 may be configured to store information utilizing one or more magnetic, inductive, and/or optical means (e.g., magnetic, inductive, and/or optical-encoding). The data storage medium 646, depicted as a first data storage medium 646*a* for example (e.g., breakout cross-section "A"), may comprise one or more of a polymer layer 646*a*-1, a magnetic data storage layer 646*a*-2, a non-magnetic layer 646*a*-3, a magnetic base layer 646*a*-4, a contact layer 646*a*-5, and/or a substrate layer 646*a*-6. According to some embodiments, a magnetic read head 648*a* may be coupled and/or disposed to read data from the magnetic data storage layer 646*a*-2.

In some embodiments, the data storage medium 646, depicted as a second data storage medium 646*b* for example (e.g., breakout cross-section "B"), may comprise a plurality of data points 646*b*-2 disposed with the second data storage medium 646*b*. The data points 646*b*-2 may, in some embodiments, be read and/or otherwise interfaced with via a laser-enabled read head 648*b* disposed and/or coupled to direct a laser beam through the second data storage medium 646*b*.

In some embodiments, the second data storage device 640*b* may comprise a CD, CD-ROM, DVD, Blu-Ray™ Disc, and/or other type of optically-encoded disk and/or other storage medium that is or becomes know or practicable. In some embodiments, the third data storage device 640*c* may comprise a USB keyfob, dongle, and/or other type of flash memory data storage device that is or becomes know or practicable. In some embodiments, the fourth data storage device 640*d* may comprise RAM of any type, quantity, and/or configuration that is or becomes practicable and/or desirable. In some embodiments, the fourth data storage device 640*d* may comprise an off-chip cache, such as a Level 2 (L2) cache memory device. According to some embodiments, the fifth data storage device 640*e* may comprise an on-chip memory device, such as a Level 1 (L1) cache memory device.

The data storage devices 640*a-e* depicted in FIG. 6A, FIG. 6B, FIG. 6C, FIG. 6D, and FIG. 6E are representative of a class and/or subset of computer-readable media that are defined herein as "computer-readable memory" (e.g., non-transitory memory devices as opposed to transmission devices or media). The data storage devices 640*a-e* may generally store program instructions, algorithms, software engines, code, and/or modules that, when executed by a processing device cause a particular machine to function in accordance with one or more embodiments described herein.

Figure 7:
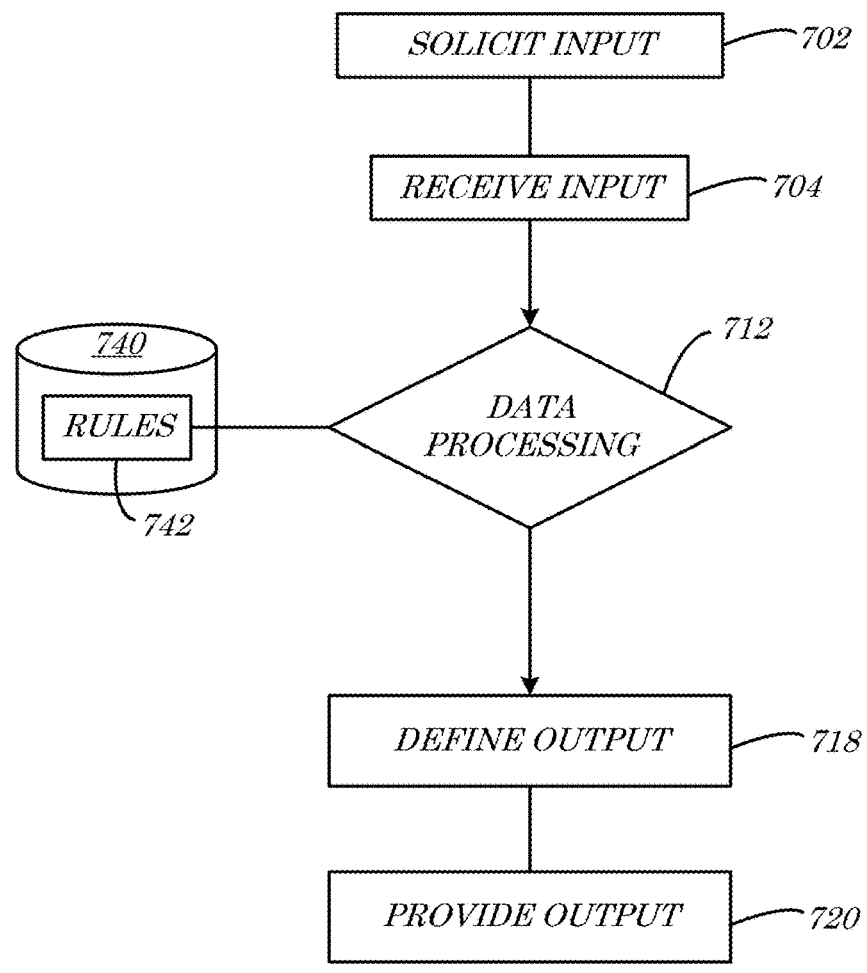
FIG. 7 is flowchart of an algorithm according to some embodiments.

With reference to FIG. 7, for example, the data storage devices 640*a-e* may store and/or define an algorithm 700. The algorithm 700 may comprise, for example, one or more software programs, modules, engines, and/or applications coded to perform the method 400 of FIG. 4 herein, and/or portions thereof. The algorithm 700, and any reference to the term "algorithm" herein, refers to any set of defined instructions that operate upon input to define and/or provide output. The algorithm 700 may, for example, be specifically programmed and/or otherwise defined to instruct a computer or other device (not shown) to solve a particular problem (e.g., logical) and/or resolve a particular mathematical calculation (e.g., arithmetic). In some embodiments, the algorithm 700 may be written and/or defined as a series or sequence of instructions encoded in (e.g., written in accordance with syntax and/or semantics rules) a particular computer programming language (e.g., Python™, Java™, JavaScript™, C, C++, C#, Basic™, FORTRAN, COBOL, Ruby™, and/or Perl™), e.g., a set of instructions that convert and/or encode characters, objects, and/or other data elements into machine code (e.g., code operable to be executed by an electronic processing device, such as a CPU).

According to some embodiments, the algorithm 700 may comprise soliciting input, at 702. Input from one or more sources may be searched for and/or queried, by structuring and/or executing a database query and/or by sending a data communication signal or "handshake", such as is common with Bluetooth® short-range communication protocols. In some embodiments, the algorithm 700 may comprise receiving the input, at 704. Whether solicited or otherwise provided and/or acquired (e.g., loaded and/or downloaded), for example, the input for the algorithm 700 may be received, identified, and/or otherwise processed and/or located. According to some embodiments, the algorithm 700 may comprise data processing, at 712. The data processing 712 may, for example, comprise execution of one or more logical and/or computational procedures, modules, scripts, and/or routines that may be stored in a memory device 740 (e.g., similar to the data storage devices 640*a-e*) as a set of instructions or rules 742 and/or that may be defined and/or implemented by one or more electrical, mechanical, and/or physical components, such as logic gates, diodes, transistors, relays, and/or switches (e.g., operable to execute the method 400 of FIG. 4 herein, and/or portions thereof).

In some embodiments, execution of the algorithm 700 may comprise a loading of the rules 742 into the memory device 740 and/or into an electronic processing system (not shown) and/or an activation of one or more logic gates and/or other electrical and/or mechanical components. The algorithm 700 may operate upon the input in accordance with the rules 742 to achieve a result by defining output, at 718. The algorithm 700 may, for example, generate, produce, define, identify, calculate, and/or otherwise compute output based on an application of the data processing 712 utilizing the rules 742 and any or all input receiving at 704. According to some embodiments, the algorithm 700 may comprise providing the output, at 720. One or more output devices (not shown) may be utilized to convey the output (e.g., a result, conclusion, decision, etc.) to one or more other devices and/or entities (not shown), such as one or more users, fire and/or safety investigators, and/or devices utilized thereby. The output may be displayed via an electronic display screen of a computer, mobile/smart phone, AR device, smart watch, etc., and/or may be transmitted as one or more electronic signals to one or more network destination addresses, such as e-mail addresses, URL locations, MAC addresses, and/or broadcast radio frequencies.

According to some embodiments, the data processing at 712 may comprise execution of a listing, sequence, matrix, and/or other set of stored steps and/or instructions that utilize the input to define the output. In some embodiments, the listing of steps and/or instruction details may comprise elements that are known to those skilled in the art. The algorithm 700 may partially or completely comprise, for example, instructions and/or steps that are well known, such as steps and/or instructions operable to calculate an area (length times width), volume (length times width times height), distance (difference between two locations), velocity (distance over time), acceleration (velocity over time), BMI, and/or any other known mathematical and/or logical (if/then statements) procedures. For any and all known procedures and/or instructions, the discrete details of such instructions are represented by the data processing at 712 and are not listed herein as one of ordinary skill in the art would readily comprehend both what such technological knowledge entails and that the inventor has possession of such knowledge. Instructions that may be included within and/or comprise the data processing at 712 (and/or the algorithm 700) may include, for example, but are not limited to, any known or practicable: (i) data transmission protocol algorithms, (ii) 3D model construction and/or generation algorithms, (iii) AR input and/or output algorithms, (iv) AI and/or ML data input classification algorithms, (v) data conversion algorithms, (vi) data encoding algorithms, (vii) data decoding algorithms, (viii) logical and/or mathematical data comparison algorithms, and (ix) data searching (e.g., keyword searching) algorithms.

VI. Rules of Interpretation

Throughout the description herein and unless otherwise specified, the following terms may include and/or encompass the example meanings provided. These terms and illustrative example meanings are provided to clarify the language selected to describe embodiments both in the specification and in the appended claims, and accordingly, are not intended to be generally limiting. While not generally limiting and while not limiting for all described embodiments, in some embodiments, the terms are specifically limited to the example definitions and/or examples provided. Other terms are defined throughout the present description.

Neither the Title (set forth at the beginning of the first page of this patent application) nor the Abstract (set forth at the end of this patent application) is to be taken as limiting in any way as the scope of the disclosed invention(s). Headings of sections provided in this patent application are for convenience only, and are not to be taken as limiting the disclosure in any way.

All definitions, as defined and used herein, should be understood to control over dictionary definitions, definitions in documents incorporated by reference, and/or ordinary meanings of the defined terms. The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

The indefinite articles "a" and "an," as used herein in the specification and in the claims, unless clearly indicated to the contrary, should be understood to mean "at least one" or "one or more". This rule applies even within the body of a claim where a first instance of an element utilizes "a" or "an" and a second or subsequent instance of the element necessarily utilizes (e.g., for purposes of proper grammar and required antecedent basis) the definite article "the" to refer to the element. The use of the definite article "the" does not limit the element to a single object merely because it is utilized to refer back to a previous mention of the element. The original reference to the element controls with respect to the plurality (or lack thereof) of the element.

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Some embodiments described herein are associated with a "user device" or a "network device". As used herein, the terms "user device" and "network device" may be used interchangeably and may generally refer to any device that can communicate via a network. Examples of user or network devices include a PC, a workstation, a server, a printer, a scanner, a facsimile machine, a copier, a Personal Digital Assistant (PDA), a storage device (e.g., a disk drive), a hub, a router, a switch, and a modem, a video game console, or a wireless phone. User and network devices may comprise one or more communication or network components. As used herein, a "user" may generally refer to any individual and/or entity that operates a user device. Users may comprise, for example, customers, consumers, product underwriters, product distributors, customer service representatives, agents, brokers, etc.

As used herein, the term "network component" may refer to a user or network device, or a component, piece, portion, or combination of user or network devices. Examples of network components may include a Static Random Access Memory (SRAM) device or module, a network processor, and a network communication path, connection, port, or cable.

In addition, some embodiments are associated with a "network" or a "communication network". As used herein, the terms "network" and "communication network" may be used interchangeably and may refer to any object, entity, component, device, and/or any combination thereof that permits, facilitates, and/or otherwise contributes to or is associated with the transmission of messages, packets, signals, and/or other forms of information between and/or within one or more network devices. Networks may be or include a plurality of interconnected network devices. In some embodiments, networks may be hard-wired, wireless, virtual, neural, and/or any other configuration of type that is or becomes known. Communication networks may include, for example, one or more networks configured to operate in accordance with the Fast Ethernet LAN transmission standard 802.3-2002® published by the Institute of Electrical and Electronics Engineers (IEEE). In some embodiments, a network may include one or more wired and/or wireless networks operated in accordance with any communication standard or protocol that is or becomes known or practicable.

As used herein, the terms "information" and "data" may be used interchangeably and may refer to any data, text, voice, video, image, message, bit, packet, pulse, tone, waveform, and/or other type or configuration of signal and/or information. Information may comprise information packets transmitted, for example, in accordance with the Internet Protocol Version 6 (IPv6) standard as defined by "Internet Protocol Version 6 (IPv6) Specification" RFC 1883, published by the Internet Engineering Task Force (IETF), Network Working Group, S. Deering et al. (December 1995). Information may, according to some embodiments, be compressed, encoded, encrypted, and/or otherwise packaged or manipulated in accordance with any method that is or becomes known or practicable.

In addition, some embodiments described herein are associated with an "indication". As used herein, the term "indication" may be used to refer to any indicia and/or other information indicative of or associated with a subject, item, entity, and/or other object and/or idea. As used herein, the phrases "information indicative of" and "indicia" may be used to refer to any information that represents, describes, and/or is otherwise associated with a related entity, subject, or object. Indicia of information may include, for example, a code, a reference, a link, a signal, an identifier, and/or any combination thereof and/or any other informative representation associated with the information. In some embodiments, indicia of information (or indicative of the information) may be or include the information itself and/or any portion or component of the information. In some embodiments, an indication may include a request, a solicitation, a broadcast, and/or any other form of information gathering and/or dissemination.

As utilized herein, the terms "program" or "computer program" may refer to one or more algorithms formatted for execution by a computer. The term "module" or "software module" refers to any number of algorithms and/or programs that are written to achieve a particular output and/or output goal—e.g., a 'login credentialing' module (or program) may provide functionality for permitting a user to login to a computer software and/or hardware resource and/or a 'shipping' module (or program) may be programmed to electronically initiate a shipment of an object via a known and/or available shipping company and/or service (e.g., FedEX®). The terms "engine" or "software engine" refer to any combination of software modules and/or algorithms that operate upon one or more inputs to define one or more outputs in an ongoing, cyclical, repetitive, and/or loop fashion. Data transformation scripts and/or algorithms that query data from a data source, transform the data, and load the transformed data into a target data repository may be termed 'data transformation engines', for example, as they repetitively operate in an iterative manner upon each row of data to produce the desired results.

Numerous embodiments are described in this patent application, and are presented for illustrative purposes only. The described embodiments are not, and are not intended to be, limiting in any sense. The presently disclosed invention(s) are widely applicable to numerous embodiments, as is readily apparent from the disclosure. One of ordinary skill in the art will recognize that the disclosed invention(s) may be practiced with various modifications and alterations, such as structural, logical, software, and electrical modifications. Although particular features of the disclosed invention(s) may be described with reference to one or more particular embodiments and/or drawings, it should be understood that such features are not limited to usage in the one or more particular embodiments or drawings with reference to which they are described, unless expressly specified otherwise.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the present invention(s). Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to the invention, and does not imply that the illustrated process is preferred.

"Determining" something can be performed in a variety of manners and therefore the term "determining" (and like terms) includes calculating, computing, deriving, looking up (e.g., in a table, database or data structure), ascertaining and the like.

It will be readily apparent that the various methods and algorithms described herein may be implemented by, e.g., appropriately and/or specially-programmed computers and/or computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software A "processor" generally means any one or more micro-processors, CPU devices, computing devices, microcon-trollers, digital signal processors, or like devices, as further described herein.

The term "computer-readable medium" refers to any medium that participates in providing data (e.g., instructions or other information) that may be read by a computer, a processor or a like device. Such a medium may take many forms, including but not limited to, non-volatile media, volatile media, and transmission media. Non-volatile media include, for example, optical or magnetic disks and other persistent memory. Volatile media include DRAM, which typically constitutes the main memory. Transmission media include coaxial cables, copper wire and fiber optics, includ-ing the wires that comprise a system bus coupled to the processor. Transmission media may include or convey acoustic waves, light waves and electromagnetic emissions, such as those generated during RF and IR data communi-cations. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, a carrier wave, or any other medium from which a computer can read.

The term "computer-readable memory" may generally refer to a subset and/or class of computer-readable medium that does not include transmission media such as wave-forms, carrier waves, electromagnetic emissions, etc. Com-puter-readable memory may typically include physical media upon which data (e.g., instructions or other informa-tion) are stored, such as optical or magnetic disks and other persistent memory, DRAM, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, computer hard drives, backup tapes, Universal Serial Bus (USB) memory devices, and the like.

Various forms of computer readable media may be involved in carrying data, including sequences of instruc-tions, to a processor. For example, sequences of instruction (i) may be delivered from RAM to a processor, (ii) may be carried over a wireless transmission medium, and/or (iii) may be formatted according to numerous formats, standards or protocols, such as Bluetooth™, TDMA, CDMA, 3G.

Where databases are described, it will be understood by one of ordinary skill in the art that (i) alternative database structures to those described may be readily employed, and (ii) other memory structures besides databases may be readily employed. Any illustrations or descriptions of any sample databases presented herein are illustrative arrange-ments for stored representations of information. Any number of other arrangements may be employed besides those suggested by, e.g., tables illustrated in drawings or else-where. Similarly, any illustrated entries of the databases represent exemplary information only; one of ordinary skill in the art will understand that the number and content of the entries can be different from those described herein. Further, despite any depiction of the databases as tables, other formats (including relational databases, object-based models and/or distributed databases) could be used to store and manipulate the data types described herein. Likewise, object methods or behaviors of a database can be used to imple-ment various processes, such as the described herein. In addition, the databases may, in a known manner, be stored locally or remotely from a device that accesses data in such a database.

The present invention can be configured to work in a network environment including a computer that is in com-munication, via a communications network, with one or more devices. The computer may communicate with the devices directly or indirectly, via a wired or wireless medium such as the Internet, LAN, WAN or Ethernet, Token Ring, or via any appropriate communications means or combination of communications means. Each of the devices may comprise computers, such as those based on the Intel® Pentium® or Centrino™ processor, that are adapted to communicate with the computer. Any number and type of machines may be in communication with the computer.

The present disclosure provides, to one of ordinary skill in the art, an enabling description of several embodiments and/or inventions. Some of these embodiments and/or inventions may not be claimed in the present application, but may nevertheless be claimed in one or more continuing applications that claim the benefit of priority of the present application. Applicants intend to file additional applications to pursue patents for subject matter that has been disclosed and enabled but not claimed in the present application.

It will be understood that various modifications can be made to the embodiments of the present disclosure herein without departing from the scope thereof. Therefore, the above description should not be construed as limiting the disclosure, but merely as embodiments thereof. Those skilled in the art will envision other modifications within the scope of the invention as defined by the claims appended hereto.

What is claimed is:

1. A system for Artificial Intelligence (AI) construction of an interactive three-dimensional (3D) human body model, comprising:

a 3D human body model controller comprising a plurality of electronic processing devices;

an Augmented Realty (AR) device in communication with the 3D human body model controller, the AR device comprising an onboard processing device, an AR out-put device in communication with the onboard pro-cessing device, and an onboard non-transitory memory device in communication with the onboard processing device, the onboard non-transitory memory device stor-ing a 3D human body model rendering program; and a non-transitory data storage device in communication with the 3D human body model controller, the non-transitory data storage device storing a medical record Large Language Model (LLM);

and wherein at least one of the non-transitory memory device and the non-transitory data storage device store instructions that when executed by at least one of the 3D human body model controller and the AR device, result in:

identifying, by the 3D human body model controller, a set of medical records for an individual;

computing, by an execution of the medical record LLM by the 3D human body model controller, and by utilizing the set of medical records for the individual as input, a plurality of medical record data elements descriptive of discrete medical record events for the individual;

populating, by an execution of the medical record LLM by the 3D human body model controller, and utiliz-ing the plurality of medical record data elements, a 3D human body model medical record data structure that maps each discrete medical record event to a specific portion of a body of the individual;

receiving, by the onboard processing device of the AR device, a request to generate a 3D human body model representing the individual;

generating, by an execution of the 3D human body model rendering program by the onboard processing device of the AR device, and utilizing the populated 3D human body model medical record data structure, a 3D human body model representing the individual;

outputting, via the AR output device, a representation of the 3D human body model disposed in an AR environment in a field of view of the AR device, wherein the outputting of the representation of the 3D human body model disposed in the AR environment in the field of view of the AR device, comprises:

(a) identifying, by an execution of the medical record LLM by the 3D human body model controller, and based on a first scaled medical image, a length and a width of the first body part of the individual;

(b) selecting, by the onboard processing device of the AR device, a default 3D human body model defining a default length and width for a 3D human body model body part corresponding to the first body part; and (c) scaling, by an execution of the 3D human body model rendering program by the onboard processing device of the AR device and based on the length and the width of the first body part of the individual, the default length and width for the 3D human body model body part corresponding to the first body part;

outputting, via the AR output device and at an AR location corresponding to a first body part of the individual, a representation of a first one of the discrete medical record events for the individual;

receiving, by the onboard processing device of the AR device, an indication of a selection of the first body part of the individual; and outputting, via the AR output device and in response to the receiving of the indication of the selection of the first body part of the individual, a representation of a first one of the plurality of medical record data elements corresponding to the first one of the discrete medical record events for the individual, wherein (i) the first one of the plurality of medical record data elements corresponding to the first one of the discrete medical record events for the individual comprises a second scaled medical image of the first body part of the individual, and (ii) the outputting of the representation of the first one of the plurality of medical record data elements corresponding to the first one of the discrete medical record events for the individual comprises superimposing the second scaled medical image on the 3D human body model at the AR location corresponding to the first body part of the individual and in place of a corresponding portion of a surface of the 3D human body model.

2. The system of claim 1, wherein the instructions, when executed by the at least one of the 3D human body model controller and the AR device, further result in:

outputting, via the AR output device, and at an AR location adjacent to the 3D human body model, a webpage interface.

3. The system of claim 2, wherein the webpage interface comprises an interface of an insurance claim evaluation tool.

4. The system of claim 1, wherein the representation of the 3D human body model disposed in the AR environment in the field of view of the AR device, comprises: (i) a 3D human body model height and, for each of a plurality of second body parts: (ii) a body part length and (iii) a body part width.

5. The system of claim 4, wherein the outputting of the 3D human body model disposed in the AR environment in the field of view of the AR device, comprises:

identifying, by the onboard processing device of the AR device, and based on data stored in the populated 3D human body model medical record data structure, a height and a weight of the individual;

selecting, by the onboard processing device of the AR device, a default 3D human body model defining a default body model height and a default body part length and body part width for each of the plurality of body parts; and scaling, by an execution of the 3D human body model rendering program by the onboard processing device of the AR device and based on the height and weight of the individual, the default body model height and the default body part length and body part width for each of the plurality of second body parts.

6. The system of claim 5, wherein the plurality of second body parts comprises at least one arm, at least on leg, and a torso.

7. The system of claim 1, wherein the first one of the discrete medical record events for the individual occurred at a first time and the representation of the 3D human body model disposed in the AR environment in the field of view of the AR device comprises a representation of the body of the individual at the first time, wherein the instructions, when executed by the at least one of the 3D human body model controller and the AR device, further result in:

outputting, via the AR output device, and at an AR location adjacent to the 3D human body model, a timeline interface comprising representation of the first time and a second time;

receiving, by the onboard processing device of the AR device, an indication of a selection of the second time; and outputting, via the AR output device and at an AR location corresponding to a second body part of the individual, a representation of a second one of the discrete medical record events for the individual that occurred at the second time.

8. The system of claim 7, wherein the outputting of the 3D human body model disposed in the AR environment in the field of view of the AR device, comprises:

identifying, by an execution of the medical record LLM by the 3D human body model controller, and based on data stored in the populated 3D human body model medical record data structure, a first length and a first width of the first body part of the individual at the first time;

outputting, via the AR output device and at an AR location corresponding to the first body part of the individual, a first representation of the first body part comprising the first length and the first width of the first body part of the individual at the first time;

identifying, by an execution of the medical record LLM by the 3D human body model controller, and based on data stored in the populated 3D human body model medical record data structure, a second length and a second width of the first body part of the individual at the second time;

modifying, by an execution of the 3D human body model rendering program by the onboard processing device of the AR device and based on the second length and the second width of the first body part of the individual at the second time, the first representation of the first body part; and outputting, via the AR output device and at an AR location corresponding to the first body part of the individual and in response to the receiving of the indication of the selection of the second time, a second representation of the first body part comprising the second length and the second width of the first body part of the individual at the second time.

9. The system of claim 1, wherein the 3D human body model comprises a wireframe avatar representing the individual and wherein the AR device comprises an AR headset.

10. The system of claim 1, wherein the generating is conducted in response to the receiving of the request to generate the 3D human body model representing the individual.

11. The system of claim 1, wherein the non-transitory memory device and the non-transitory data storage device comprise different devices.

12. The system of claim 1, wherein the identifying comprises:

receiving, by the 3D human body model controller and from a user device, and indication of an identity of the individual.

13. The system of claim 1, wherein the set of medical records for the individual comprises a plurality of image, semi-structured data, and text files.

14. The system of claim 13, wherein the instructions, when executed by the at least one of the 3D human body model controller and the AR device, further result in:

converting, by the 3D human body model controller, the set of medical records for an individual into text format.

15. The system of claim 14, wherein the converting comprises executing an OCR algorithm.

16. The system of claim 1, wherein the medical record LLM comprises an LLM trained to recognize and categorize medical data represented in textual form.

17. The system of claim 1, wherein the medical record LLM comprises an LLM trained to recognize and categorize medical data represented in image form.

18. The system of claim 1, wherein the superimposing of the second scaled medical image on the 3D human body model at the AR location corresponding to the first body part of the individual comprises mapping the second scaled medical image to the 3D human body model in place of the corresponding portion of the surface of the 3D human body model.

19. The system of claim 1, wherein the superimposing of the second scaled medical image on the 3D human body model at the AR location corresponding to the first body part of the individual comprises stitching the second scaled medical image to the 3D human body model in place of the corresponding portion of the surface of the 3D human body model.

* * * * *